(12) United States Patent
Kitamura et al.

(10) Patent No.: US 9,375,133 B2
(45) Date of Patent: Jun. 28, 2016

(54) ENDOSCOPIC OBSERVATION SUPPORT SYSTEM

(75) Inventors: Yoshiro Kitamura, Tokyo (JP); Keigo Nakamura, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 512 days.

(21) Appl. No.: 13/638,812

(22) PCT Filed: Mar. 30, 2011

(86) PCT No.: PCT/JP2011/001932
§ 371 (c)(1),
(2), (4) Date: Oct. 1, 2012

(87) PCT Pub. No.: WO2011/122032
PCT Pub. Date: Oct. 6, 2011

(65) Prior Publication Data
US 2013/0023730 A1 Jan. 24, 2013

(30) Foreign Application Priority Data

Mar. 31, 2010 (JP) .................. 2010-083603

(51) Int. Cl.
*A61B 1/00* (2006.01)
*A61B 6/12* (2006.01)
(Continued)

(52) U.S. Cl.
CPC ........... *A61B 1/00055* (2013.01); *A61B 1/0005* (2013.01); *A61B 1/00009* (2013.01);
(Continued)

(58) Field of Classification Search
CPC ........... A61B 19/5225; A61B 1/00009; A61B 1/0005; A61B 1/00055; A61B 1/3132; A61B 2019/5255; A61B 2019/5291; A61B 5/064; A61B 6/032; A61B 6/12; A61B 6/466; A61B 6/486; A61B 6/5211
USPC .................. 600/104, 111, 124, 424–427, 476
See application file for complete search history.

(56) References Cited

U.S. PATENT DOCUMENTS

2002/0128547 A1 9/2002 Furuhashi et al.
2005/0033117 A1 2/2005 Ozaki et al.
(Continued)

FOREIGN PATENT DOCUMENTS

CN 101322652 12/2008
EP 2123215 A1 11/2009
(Continued)

OTHER PUBLICATIONS

Jianmin et al., Computer Simulation Scaling Biopsy Method and Apparatus, Dec. 17, 2008; English machine translated document of CN 101322652 (A).*
(Continued)

*Primary Examiner* — John P Leubecker
*Assistant Examiner* — Arnaldo Torres Diaz
(74) *Attorney, Agent, or Firm* — Young & Thompson

(57) ABSTRACT

A virtual field of view of a virtual endoscope, which is positioned at a position corresponding to a detected position of an endoscope in a 3D medical image, is determined based on a position of a structure of interest, the corresponding position and a posture of the endoscope, and an angle of view of the endoscope, such that the position of the structure of interest is contained within the virtual field of view and the virtual field of view has continuity with the field of view of the endoscope. From the 3D medical image inputted, a virtual endoscopic image having the determined virtual field of view with the view point thereof being the corresponding position of the endoscope is generated. The generated virtual endoscopic image is displayed on a WS display.

15 Claims, 21 Drawing Sheets

(51) Int. Cl.
*A61B 1/313* (2006.01)
*A61B 5/06* (2006.01)
*A61B 19/00* (2006.01)
*A61B 6/03* (2006.01)
*A61B 6/00* (2006.01)

(52) U.S. Cl.
CPC ............. *A61B1/3132* (2013.01); *A61B 6/12* (2013.01); *A61B 6/5211* (2013.01); *A61B 5/064* (2013.01); *A61B 6/032* (2013.01); *A61B 6/466* (2013.01); *A61B 6/486* (2013.01); *A61B 19/5225* (2013.01); *A61B 2019/5255* (2013.01); *A61B 2019/5291* (2013.01)

(56) References Cited

U.S. PATENT DOCUMENTS

| | | | |
|---|---|---|---|
| 2005/0215879 A1* | 9/2005 | Chuanggui | 600/407 |
| 2007/0173689 A1 | 7/2007 | Ozaki et al. | |
| 2008/0207997 A1* | 8/2008 | Higgins et al. | 600/114 |
| 2008/0247619 A1 | 10/2008 | Li | |
| 2008/0287783 A1* | 11/2008 | Anderson | 600/429 |
| 2009/0156895 A1* | 6/2009 | Higgins et al. | 600/104 |
| 2009/0278920 A1 | 11/2009 | Kamo | |
| 2009/0292171 A1 | 11/2009 | Ito | |
| 2010/0295931 A1* | 11/2010 | Schmidt | 348/65 |
| 2011/0015649 A1* | 1/2011 | Anvari et al. | 606/130 |
| 2011/0060216 A1* | 3/2011 | Foley et al. | 600/426 |
| 2011/0152692 A1* | 6/2011 | Nie et al. | 600/473 |
| 2011/0172526 A1* | 7/2011 | Lachaine et al. | 600/439 |
| 2011/0230710 A1* | 9/2011 | Hoeg et al. | 600/103 |
| 2011/0319751 A1* | 12/2011 | Groszmann | 600/424 |
| 2012/0069167 A1* | 3/2012 | Liu et al. | 348/65 |

FOREIGN PATENT DOCUMENTS

| | | |
|---|---|---|
| JP | 11-000309 | 1/1999 |
| JP | 2002-263053 | 9/2002 |
| JP | 2005-021353 | 1/2005 |
| JP | 2005-211529 | 8/2005 |
| JP | 2006-198032 | 8/2006 |
| JP | 2006-230906 | 9/2006 |
| JP | 2008-245719 | 10/2008 |
| JP | 2009-276371 | 11/2009 |

OTHER PUBLICATIONS

International Search Report, PCT/JP2011/001932, Jul. 12, 2011.
Chinese Office Action dated Aug. 5, 2014, in corresponding Chinese Patent Application No. 201180016415.2.
CN Office Action dated May 11, 2015, with an English translation; Application No. 201180016415.2.
Extended European Search Report, dated Oct. 14, 2015, Application No. 11762274.6.

* cited by examiner

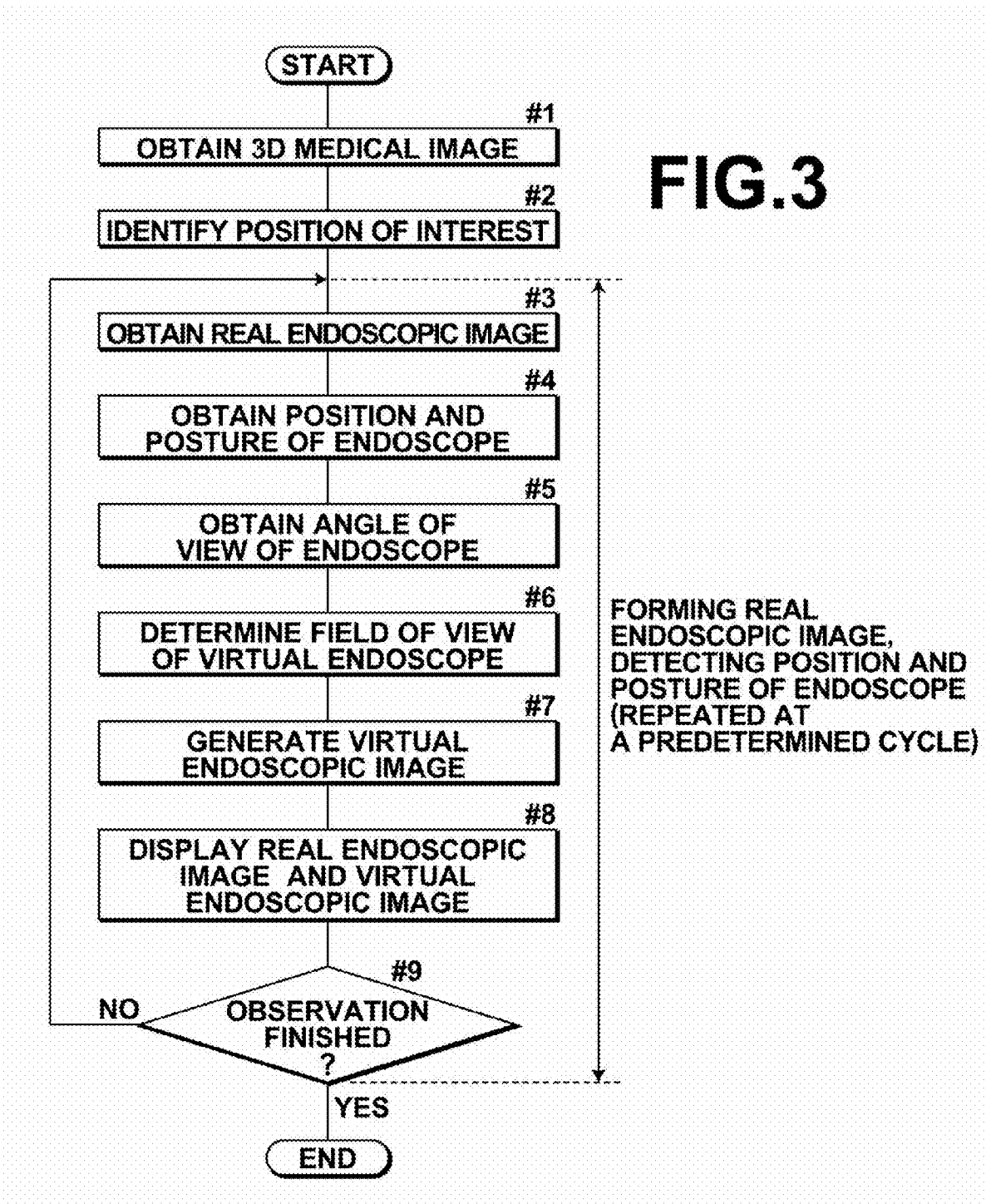

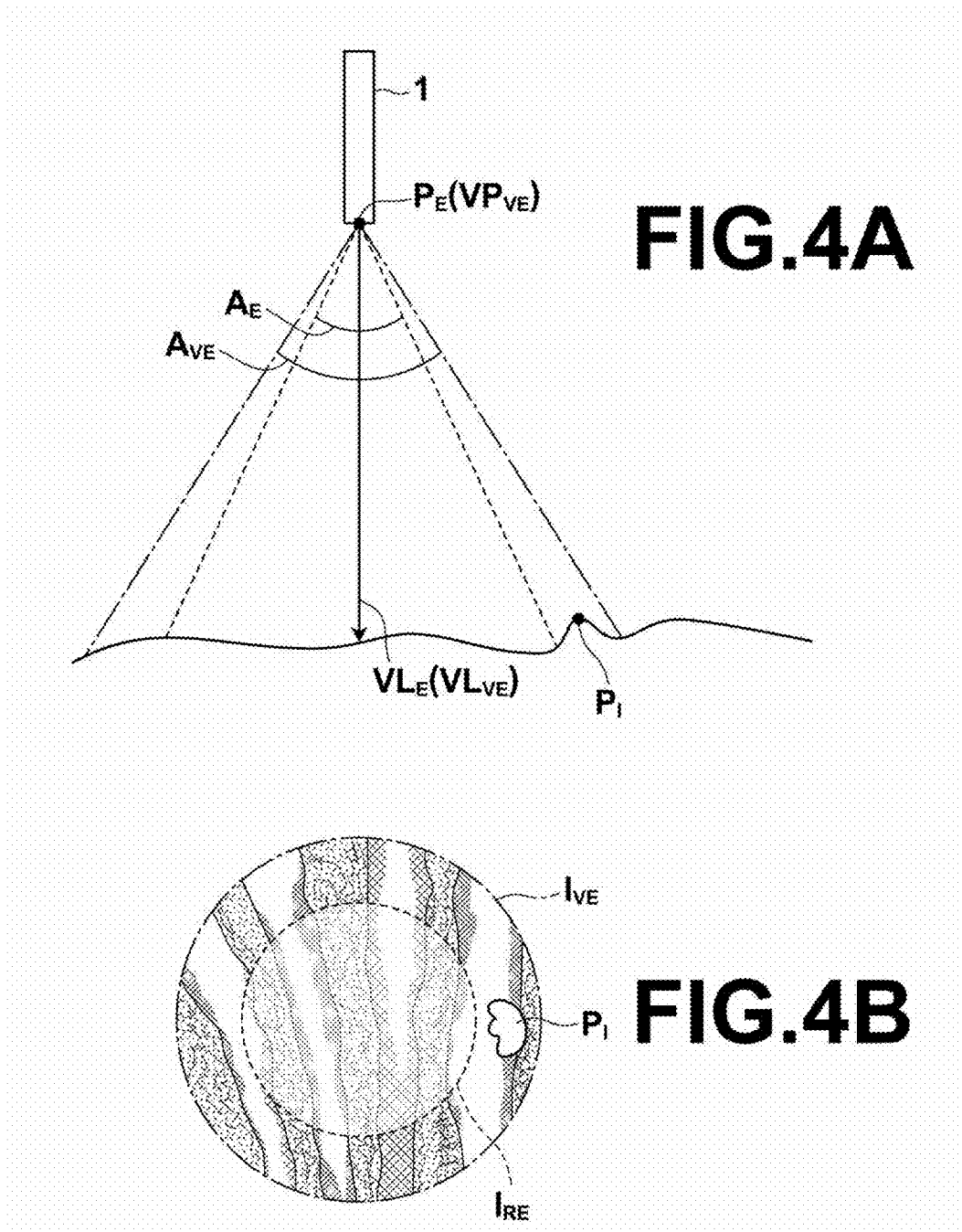

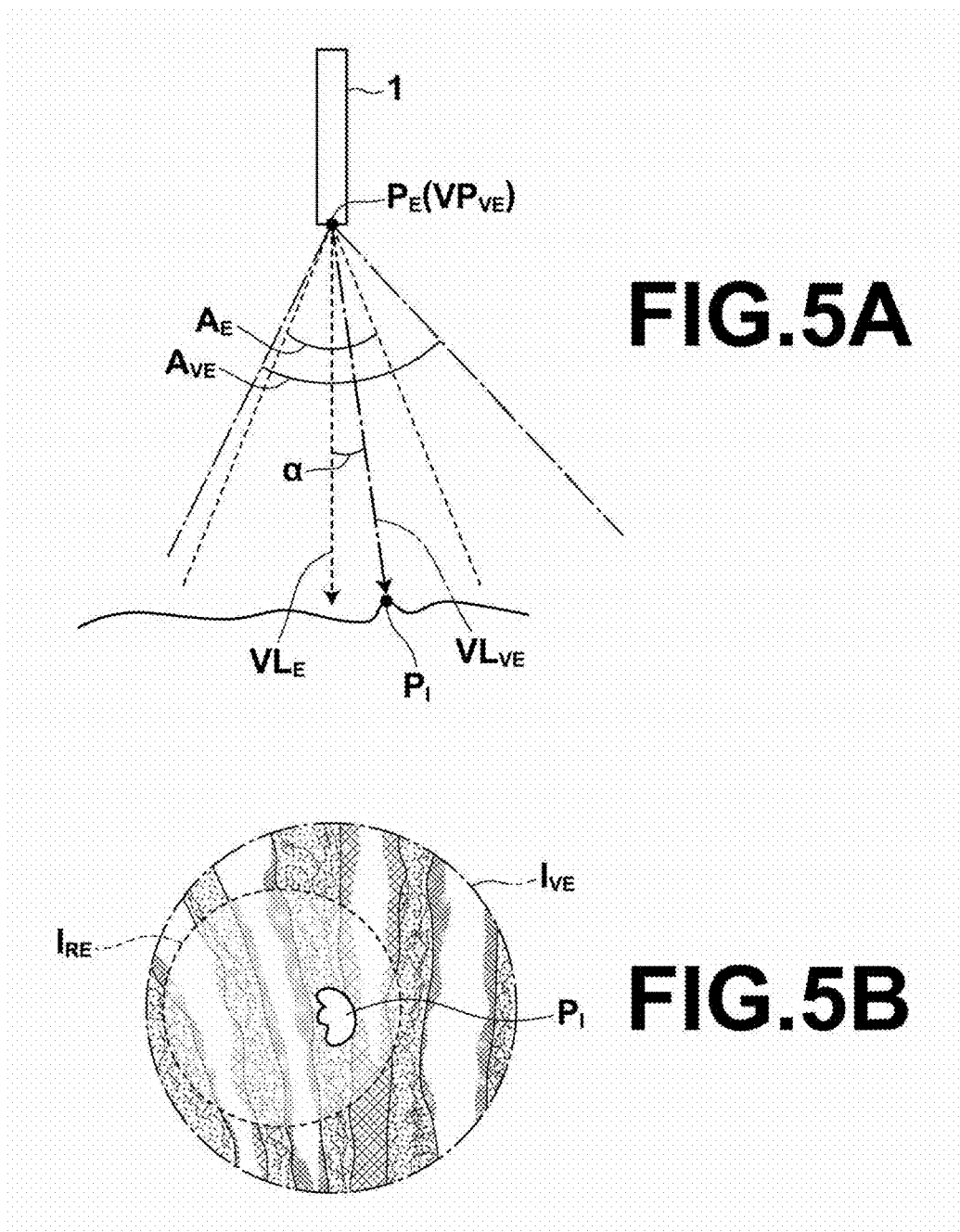

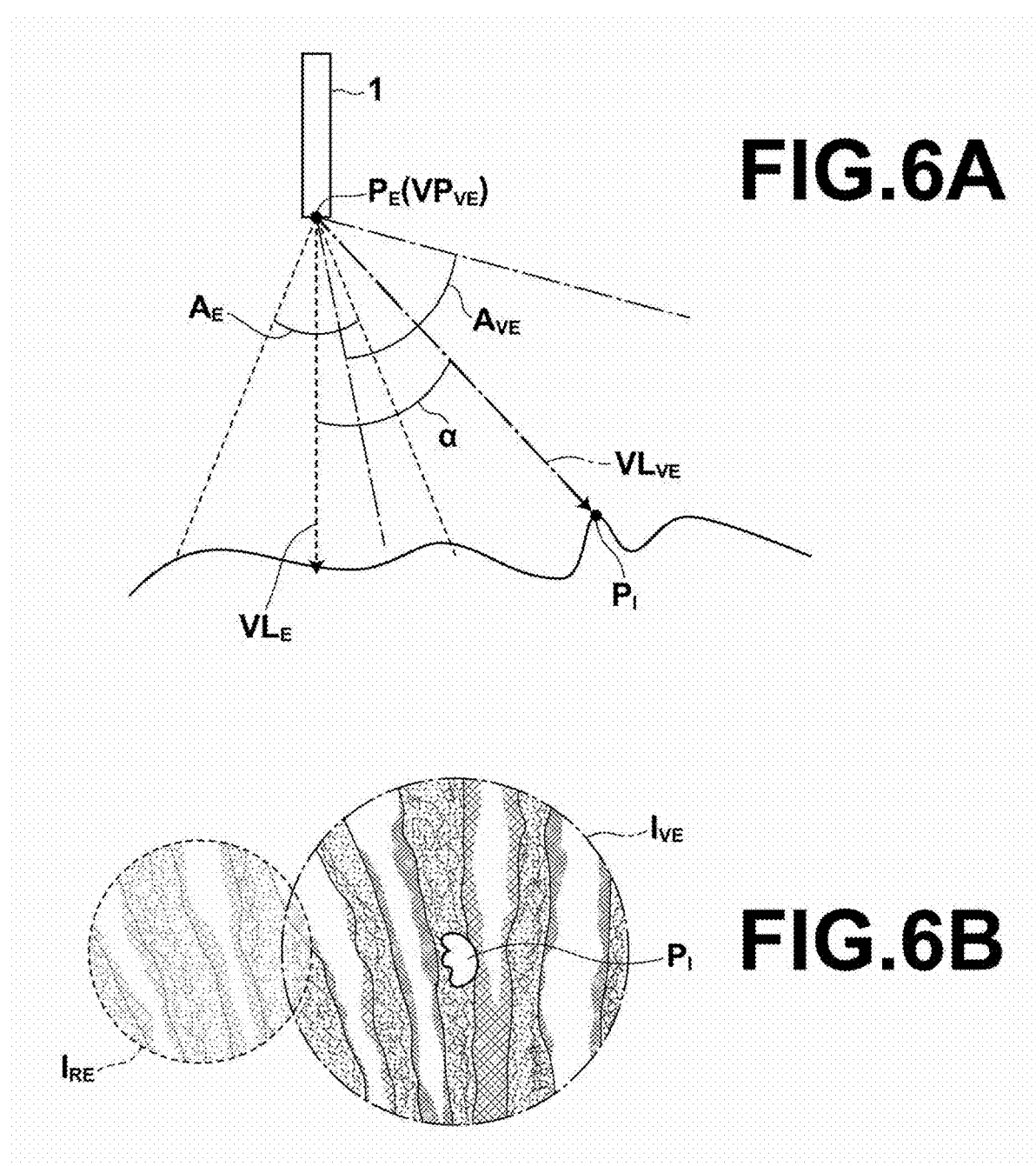

ENDOSCOPIC OBSERVATION SUPPORT SYSTEM

BACKGROUND OF THE INVENTION

1. Field of the Invention

The present invention relates to a technology for supporting endoscopic observation during surgery or examination using an endoscope inserted in a body cavity of a subject, and in particular to a technology for supporting endoscopic observation using a virtual endoscopic image representing the interior of a body cavity of a subject.

2. Description of the Related Art

In recent years, surgery using an endoscope, such as laparoscopic surgery and thoracoscopic surgery, is drawing attention. The endoscopic surgery is advantageous in that it does not require laparotomy, thoracotomy, or the like, and only needs to make two or three holes of few centimeters in diameter for insertion of an endoscope and a surgical tool, thereby significantly reducing the burden imposed on the patient. However, conducting surgery with a very limited field of view of the endoscope is highly difficult, and doctors require a lot of skill to conduct the endoscopic surgery. If a blood vessel or an organ of the patient is damaged by mistake and breeds during the endoscopic surgery, it is impossible to continue the endoscopic surgery and the doctor has to conduct conventional surgery involving laparotomy, thoracotomy, or the like.

On the other hand, a virtual endoscopy technology for generating a virtual endoscopic image, which is similar to an endoscopic image, from a 3D volume image taken with a CT device, or the like, is known. This technology is widely used in North America as a method for finding a tumor, in particular, a colorectal tumor, only by CT imaging without conducting endoscopic examination.

Further, a technology for supporting endoscopic surgery using a virtual endoscopic image has been proposed.

For example, Japanese Unexamined Patent Publication No. 2002-263053 (hereinafter, Patent Document 1) has disclosed a device that detects a position of an endoscope with a sensor, generates a virtual endoscopic image having an angle of view wider than that of the endoscope with setting the detected position of the endoscope as a view point, and displays the virtual endoscopic image and a real endoscopic image taken with the endoscope superimposed one on the other.

Further, Japanese Unexamined Patent Publication No. 2005-021353 (hereinafter, Patent Document 2) has disclosed a device that detects a real-time position of an endoscope to generate a virtual endoscopic image having the same field of view as that of the endoscope, where location of blood vessels in the field of view is visualized. The device also detects a real-time position of a surgical tool used during endoscopic surgery to generate a composite image in which an image representing the surgical tool is combined at the position of the surgical tool in the virtual endoscopic image, and displays the composite image and a real endoscopic image.

According to the techniques disclosed in these documents, however, although the virtual endoscopic image serves to compensate for the narrow field of view of the endoscope, the virtual endoscopic image has the same viewpoint as that of the real endoscopic image, i.e., is an image viewed from the same observation direction as that of the real endoscopic image. Therefore, depending on the positional relationship between the endoscope and a site of interest, such as a surgical tool or a site of surgical interest, the site of interest may not sometimes be shown in the virtual endoscopic image and the real endoscopic image, and the doctor cannot recognize the approach of the endoscope to the site of interest in such a case.

SUMMARY OF THE INVENTION

In view of the above-described circumstances, the present invention is directed to providing a system, a method, a device and a program for allowing the user to more reliably recognize a positional relationship between an endoscope and a site of interest, such as a surgical tool or a site of surgical interest, and the approach of the endoscope to the site of interest during observation of a body cavity of a subject using the endoscope inserted in the body cavity.

An aspect of an endoscopic observation support system of the invention includes: 3D medical image forming means for forming a 3D medical image representing an interior of a body cavity of a subject; position of interest identifying means for identifying a position of a (first) structure of interest in the body cavity in the 3D medical image; endoscope position and posture detecting means for detecting a real-time position and a real-time posture of an endoscope inserted in the body cavity; endoscope angle of view obtaining means for obtaining information of an angle of view of the endoscope; virtual field of view determining means for determining a virtual field of view of a virtual endoscope positioned at an endoscope-corresponding position, the endoscope-corresponding position being a position in the 3D medical image corresponding to the detected position of the endoscope, based on the identified position of the (first) structure of interest, the detected position and posture of the endoscope in the 3D medical image, and the angle of view of the endoscope, such that the position of the (first)) structure of interest is contained within the virtual field of view and the virtual field of view has continuity with an endoscope-corresponding field of view, the endoscope-corresponding field of view being a field of view of the 3D medical image corresponding to a field of view of the endoscope; virtual endoscopic image generating means for generating, from the 3D medical image inputted thereto, a virtual endoscopic image having the virtual field of view with a view point thereof being the endoscope-corresponding position; and display means for displaying the virtual endoscopic image.

An aspect of an endoscopic observation support method of the invention includes the steps of: forming a 3D medical image representing an interior of a body cavity of a subject before or during endoscopic observation of the interior of the body cavity with an endoscope inserted in the body cavity; identifying a position of a (first) structure of interest in the body cavity in the 3D medical image; detecting a real-time position and a real-time posture of the endoscope inserted in the body cavity; obtaining information of an angle of view of the endoscope; determining a virtual field of view of a virtual endoscope positioned at an endoscope-corresponding position, the endoscope-corresponding position being a position in the 3D medical image corresponding to the detected position of the endoscope, based on the identified position of the (first) structure of interest, the detected position and posture of the endoscope in the 3D medical image, and the angle of view of the endoscope, such that the position of the (first) structure of interest is contained within the virtual field of view and the virtual field of view has continuity with an endoscope-corresponding field of view, the endoscope-corresponding field of view being a field of view of the 3D medical image corresponding to a field of view of the endoscope; generating, from the 3D medical image inputted, a virtual endoscopic image having the virtual field of view with a view point thereof being the endoscope-corresponding position, the virtual endoscopic image representing the interior of the body cavity viewed from the view point; and displaying the virtual endoscopic image.

An aspect of an endoscopic observation support device of the invention includes: 3D medical image obtaining means for obtaining a 3D medical image representing an interior of a body cavity of a subject; position of interest identifying means for identifying a position of a (first) structure of interest in the body cavity in the 3D medical image; position obtaining means for obtaining a real-time position and a real-time posture of an endoscope inserted in the body cavity detected by position and posture detecting means; endoscope angle of view obtaining means for obtaining information of an angle of view of the endoscope; virtual field of view determining means for determining a virtual field of view of a virtual endoscope positioned at an endoscope-corresponding position, the endoscope-corresponding position being a position in the 3D medical image corresponding to the detected position of the endoscope, based on the identified position of the (first) structure of interest, the obtained position and posture of the endoscope in the 3D medical image, and the angle of view of the endoscope, such that the position of the (first) structure of interest is contained within the virtual field of view and the virtual field of view has continuity with an endoscope-corresponding field of view, the endoscope-corresponding field of view being a field of view of the 3D medical image corresponding to a field of view of the endoscope; virtual endoscopic image generating means for generating, from the 3D medical image inputted thereto, a virtual endoscopic image having the virtual field of view with a view point thereof being the endoscope-corresponding position; and display control means for causing display means to display the virtual endoscopic image.

An aspect of an endoscopic observation support program of the invention causes a computer to carry out the steps of: obtaining a 3D medical image representing an interior of a body cavity of a subject; identifying a position of a (first) structure of interest in the body cavity in the 3D medical image; obtaining a real-time position and a real-time posture of an endoscope inserted in the body cavity detected by position and posture detecting means; obtaining information of an angle of view of the endoscope; determining a virtual field of view of a virtual endoscope positioned at an endoscope-corresponding position, the endoscope-corresponding position being a position in the 3D medical image corresponding to the detected position of the endoscope, based on the identified position of the (first) structure of interest, the detected position and posture of the endoscope in the 3D medical image, and the angle of view of the endoscope, such that the position of the (first) structure of interest is contained within the virtual field of view and the virtual field of view has continuity with an endoscope-corresponding field of view, the endoscope-corresponding field of view being a field of view of the 3D medical image corresponding to a field of view of the endoscope; generating, from the 3D medical image inputted, a virtual endoscopic image having the virtual field of view with a view point thereof being the endoscope-corresponding position; and causing display means to display the virtual endoscopic image.

Now, details of the invention are described.

In the invention, a real endoscopic image representing the interior of the body cavity may be formed by real-time imaging with the endoscope, and the virtual endoscopic image and the real endoscopic image which is formed almost at the same time when the position and posture of the endoscope used to generate the virtual endoscopic image are detected may be displayed with being superimposed one on the other and corresponding positions between the virtual endoscopic image and the real endoscopic image being aligned with each other. In this manner, the real endoscopic image, which is formed real-time by imaging with the endoscope, and the virtual endoscopic image, which is viewed from the real-time position of the endoscope detected by the position and posture detecting means almost at the same time when the real endoscopic image is formed, are displayed with being superimposed one on the other.

In a case where the generation of the virtual endoscopic image is repeated in response to detection of the position and posture of the endoscope, real-time update of both the real endoscopic image and the virtual endoscopic image along with movement of the endoscope is achieved.

In the invention, in a case where the 3D medical image is formed and obtained during observation using the endoscope, the 3D medical image may be obtained real-time. In this case, the position and posture of the endoscope may be detected by performing image recognition processing on the obtained 3D medical image.

Specific examples of the "(first) structure of interest" may include a site of surgical interest during endoscopic surgery and an anatomical structure that requires attention during endoscopic surgery, such as a blood vessel, an organ or a tumor. A specific method for identifying the position of the (first) structure of interest may be an automatic method using a known image recognition technique, a method involving manual operation by the user, or a method combining both the automatic and manual methods. Alternatively, the "(first) structure of interest" may be a surgical tool inserted in the body cavity.

The "virtual field of view" is determined such that the position of the (first) structure of interest is contained within the field of view. This means that image information along a line of sight from the viewpoint (the position of the endoscope) toward the position of the (first) structure of interest is reflected in the virtual endoscopic image. If, for example, a structure, such as an organ, a blood vessel or a fold, is present between the endoscope and the (first) structure of interest, the (first) structure of interest may not necessarily be shown in the virtual endoscopic image.

Further, the "virtual field of view" has continuity with the field of view of the endoscope. The description "the virtual field of view (of the virtual endoscopic image) has continuity with the field of view of the endoscope" means that these fields of view contact with each other at least one point. Specifically, one of the fields of view may be contained within the other of the fields of view, the fields of view may partially overlap with each other, or the fields of view may entirely overlap with each other.

The "virtual field of view" may have an angle of view wider than that of the endoscope.

In the "virtual endoscopic image", the (first) structure of interest may be shown in an identifiable manner.

When the "virtual endoscopic image" is generated, a distance from the endoscope to a surface of a structure in the body cavity may be used as a determinant of pixel values of the virtual endoscopic image. Alternatively, a color template, which is defined to provide the virtual endoscopic image showing sites in the body cavity in almost the same appearance as those shown in the real endoscopic image, may be used. It should be noted that the color template may include, for example, one that is defined such that each site in the body cavity has almost the same color of as that shown in the real endoscopic image, and each site in the body cavity may be shown semitransparent, as necessary, so that a structure behind an obstacle, which cannot be observed in the real endoscopic image, is visually recognizable in the virtual endoscopic image.

In the invention, a second structure of interest in the body cavity in the 3D medical image may be detected, and the virtual endoscopic image showing the detected second structure of interest in a visually recognizable manner may be generated. Specific examples of the "second structure of interest" may include those mentioned above with respect to the first structure of interest. Therefore, for example, the first structure may be a site of surgical interest during endoscopic surgery and the second structure of interest may be an anatomical structure that requires attention during the surgery, or vice versa.

In the invention, a warning may be shown when the approach of the endoscope to the (first) structure of interest satisfies a predetermined criterion. The warning may be visually shown in the virtual endoscopic image, or may be shown in a manner perceived by any other sense organ.

According to the invention, from an inputted 3D medical image, which shows the interior of a body cavity of a subject, a virtual endoscopic image is generated and displayed, where the view point of the virtual endoscopic image is a position in the 3D medical image corresponding to a position of an endoscope detected by position and posture detecting means, the field of view of the virtual endoscopic image contains a position of the structure of interest, and the field of view of the virtual endoscopic image has continuity with the field of view of the endoscope. The field of view of the displayed virtual endoscopic image is determined such that the position of the structure of interest is always contained in the field of view, thereby allowing the user to reliably recognize the positional relationship and the approach between the endoscope and the structure of interest, and helping to prevent misoperation, etc., during surgery or examination. Further, the field of view of the virtual endoscopic image has continuity with the field of view of the endoscope. This facilitates the user to recognize the positional relationship between these fields of view. For example, even when the structure of interest is not contained in the real endoscopic image, the user can easily recognize how the endoscope should be moved to make the structure of interest be contained in the field of view of the real endoscopic, and this improves operability of the endoscope during surgery.

Further, at this time, the view point and the field of view of the virtual endoscope of the continuously displayed virtual endoscopic image are changed real-time by feedback of the detected real-time position of the endoscope. This allows the user to dynamically and more appropriately recognize the approach of the endoscope to the structure of interest.

Still further, in the case where the real endoscopic image representing the interior of the body cavity is formed by real-time imaging with the endoscope, and the virtual endoscopic image and the real endoscopic image which is formed almost at the same time when the position and posture of the endoscope used to generate the virtual endoscopic image are detected are displayed with being superimposed one on the other and corresponding positions between the virtual endoscopic image and the real endoscopic image being aligned with each other, the displayed real endoscopic image and virtual endoscopic image show the state of the interior of the body cavity almost at the same point of time, and thus the real endoscopic image and the virtual endoscopic image are continuously displayed in a temporally synchronized manner. Yet further, in the case where the generation of the virtual endoscopic image is repeated in response to detection of the position of the endoscope, real-time update of both the real endoscopic image and the virtual endoscopic image is achieved. That is, the field of view of the real endoscopic image changes along with movement or rotation of the endoscope, and the field of view of the virtual endoscopic image changes along with movement, etc., of the endoscope. In this manner, the user can observe the interior of the body cavity with complementary using the real endoscopic image and the virtual endoscopic image.

BRIEF DESCRIPTION OF THE DRAWINGS

FIG. 3 is a flow chart illustrating the flow of an endoscopic observation support process according to the first to the third embodiments of the invention, FIG. 4A is a diagram schematically illustrating one example of a field of view of a virtual endoscope, which is determined based on a field of view of a real endoscope and a position of a structure of interest, in the first embodiment of the invention, FIG. 4B is a diagram schematically illustrating one example of a superimposed display of a real endoscopic image and a virtual endoscopic image in the first embodiment of the invention, FIG. 5A is a diagram schematically illustrating a first example of the field of view of the virtual endoscope, which is determined based on the field of view of the real endoscope and the position of the structure of interest, in a modification of the first embodiment of the invention, FIG. 5B is a diagram schematically illustrating one example of the superimposed display of the real endoscopic image and the virtual endoscopic image in the case shown in FIG. 5A in the modification of the first embodiment of the invention, FIG. 6A is a diagram schematically illustrating a second example of the field of view of the virtual endoscope, which is determined based on the field of view of the real endoscope and the position of the structure of interest, in the modification of the first embodiment of the invention, FIG. 6B is a diagram schematically illustrating one example of the superimposed display of the real endoscopic image and the virtual endoscopic image in the case shown in FIG. 6A in the modification of the first embodiment of the invention.

DESCRIPTION OF THE PREFERRED EMBODIMENTS

Hereinafter, an endoscopic observation support system according to embodiments of the present invention is described.

Figure 1:
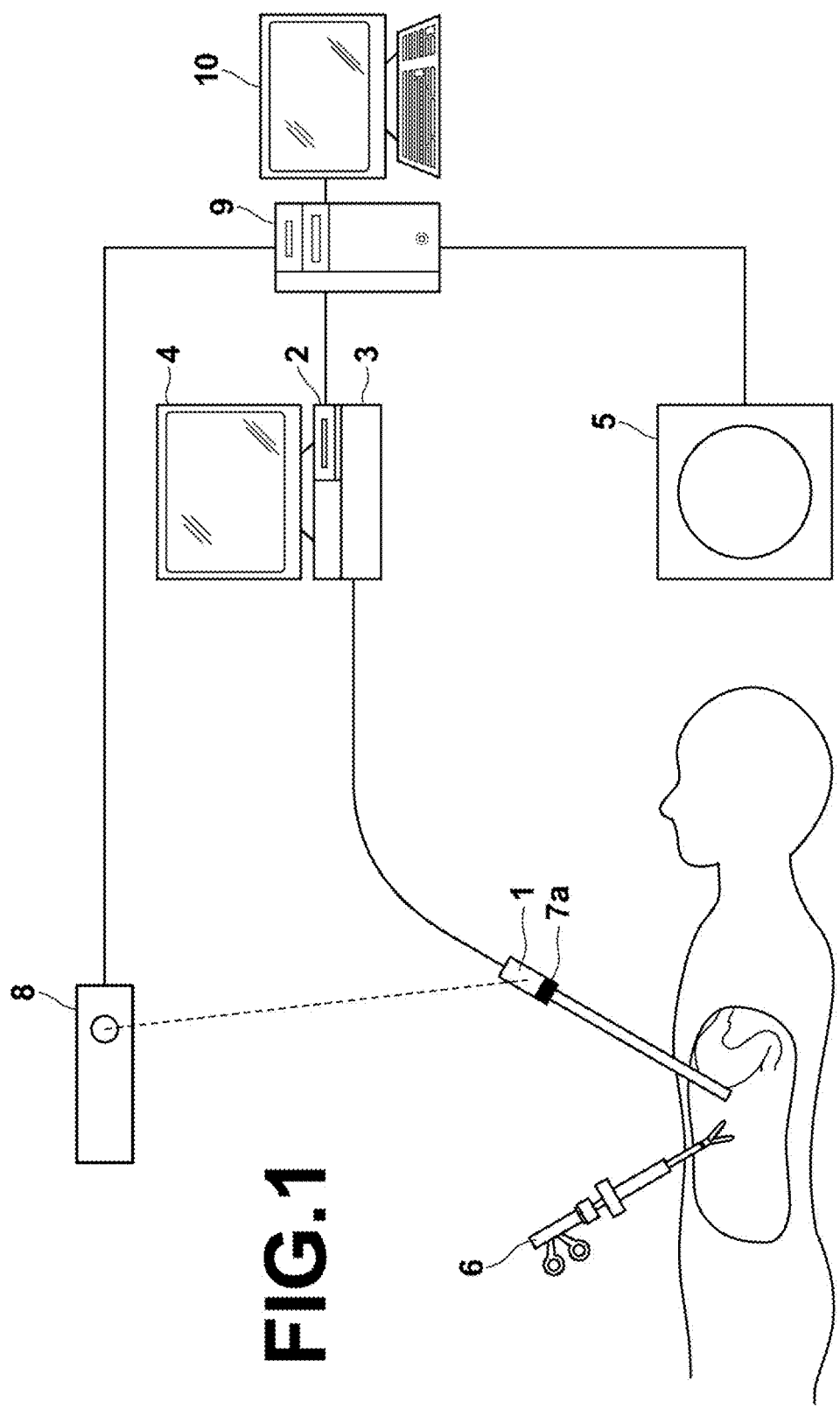
FIG. 1 is a diagram illustrating the hardware configuration of an endoscopic observation support system according to first to fifth embodiments of the present invention.

FIG. 1 is a hardware configuration diagram illustrating the outline of the endoscopic observation support system according to a first embodiment of the invention. As shown in the drawing, the system includes an endoscope 1, a digital processor 2, a light source device 3, a real endoscopic image display 4, a modality 5, a surgical tool 6, an endoscope marker 7a, a position sensor 8, an image processing workstation 9, and an image processing workstation display (which will hereinafter be referred to as "WS display") 10.

In this embodiment, the endoscope 1 is a hard endoscope for the abdominal cavity, and is inserted in the abdominal cavity of a subject. Light from the light source device 3 is guided by an optical fiber and emitted from the tip portion of the endoscope 1, and an image of the interior of the abdominal cavity of the subject is taken by an imaging optical system of the endoscope 1. The digital processor 2 converts an image signal obtained by the endoscope 1 into a digital image signal, and performs image quality correction by digital signal processing, such as white balance control and shading correction. Then, the digital processor 2 adds accompanying information prescribed by the DICOM (Digital Imaging and Communications in Medicine) standard to the digital image signal to output real endoscopic image data ($I_{RE}$). The outputted real endoscopic image data ($I_{RE}$) is sent to the image processing workstation 9 via a LAN according to a communication protocol conforming to the DICOM standard. Further, the digital processor 2 converts the real endoscopic image data ($I_{RE}$) into an analog signal and outputs the analog signal to the real endoscopic image display 4, so that the real endoscopic image ($I_{RE}$) is displayed on the real endoscopic image display 4. The endoscope 1 obtains the image signal at a predetermined frame rate, and therefore the real endoscopic image ($I_{RE}$) displayed on the real endoscope display 4 is a moving image showing the interior of the abdominal cavity. The endoscope 1 can also take a still image in response to an operation by the user.

The modality 5 is a device that images a site to be examined of the subject and generates image data (V) of a 3D medical image representing the site. In this embodiment, the modality 5 is a CT device. The 3D medical image data (V) also has the accompanying information prescribed by the DICOM standard added thereto. The 3D medical image data (V) is also sent to the image processing workstation 9 via the LAN according to the communication protocol conforming to the DICOM standard.

The endoscope marker 7a and the position sensor 8 form a known three-dimensional position measurement system. The endoscope marker 7a is provided in the vicinity of a handle of the endoscope 1, and a three-dimensional position of the marker 7a is detected by the optical position sensor 8 at predetermined time intervals. The endoscope marker 7a is formed by a plurality of marker chips, so that the position sensor 8 can also detect the posture of the endoscope 1 based on a positional relationship among the marker chips. The posture of the endoscope 1 represents an orientation of the inserted endoscope, and agrees with an orientation of a line of sight at the center of the field of view of the endoscope. Therefore, the posture of the endoscope 1 may hereinafter be referred to as a center line of sight vector of the endoscope 1. Further, a three-dimensional position $PS_E$ of the tip portion of the endoscope 1 may be calculated by an offset calculation. The position sensor 8 sends the calculated three-dimensional position data $PS_E$ and a three-dimensional posture data $DS_E$ of the endoscope 1 to the image processing workstation 9 via a USB interface.

The image processing workstation 9 is a computer having a known hardware configuration including a CPU, a main storage device, an auxiliary storage device, an input/output interface, a communication interface, a data bus, etc., to which an input device (such as a pointing device and a keyboard) and the WS display 10 are connected. The image processing workstation 9 is connected to the digital processor 2 and the modality 5 via the LAN, and to the position sensor 8 via the USB connection. The image processing workstation 9 has installed therein a known operating system, various application software programs, etc., and an application software program for executing an endoscopic observation support process of the invention. These software programs may be installed from a recording medium, such as a CD-ROM, or may be downloaded from a storage device of a server connected via a network, such as the Internet, before being installed.

Figure 2:
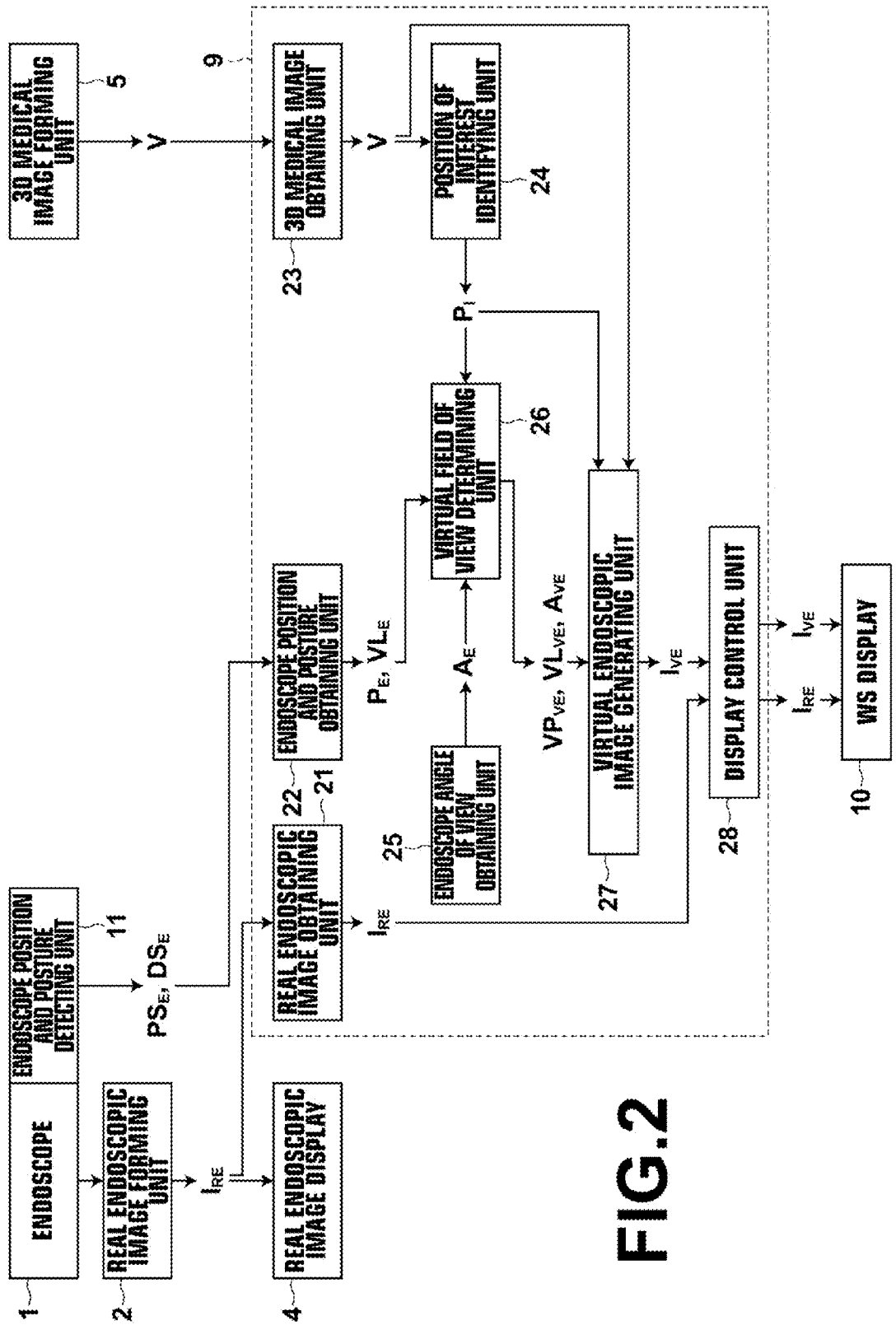
FIG. 2 is a functional block diagram of the endoscopic observation support system according to the first to the third embodiments of the invention.

FIG. 2 is a functional block diagram of the endoscopic observation support system according to a first embodiment of the invention. As shown in the drawing, the endoscopic observation support system according to the first embodiment of the invention includes the endoscope 1, a real endoscopic image forming unit 2, the real endoscopic image display 4, a 3D medical image forming unit 5, the WS display 10, an endoscope position and posture detecting unit 11, a real endoscopic image obtaining unit 21, an endoscope position and posture obtaining unit 22, a 3D medical image obtaining unit 23, a position of interest identifying unit 24, an endoscope angle of view obtaining unit 25, a virtual field of view determining unit 26, a virtual endoscopic image generating unit 27, and a display control unit 28. It should be noted that the same reference numeral as that assigned to each hardware device shown in FIG. 1 is used to denote a corresponding functional block shown in FIG. 2 when there is substantially one to one correspondence therebetween. That is, the function of the real endoscopic image forming unit 2 is implemented by the digital processor shown in FIG. 1, and the function of the 3D medical image forming unit 5 is implemented by the modality shown in FIG. 1. On the other hand, the function of the endoscope position and posture detecting unit 11 is implemented by the endoscope marker 7a and the position sensor 8. The dashed line frame represents the image processing workstation 9, and the functions of the individual processing units in the dashed line frame are implemented by executing predetermined programs on the image processing workstation 9. Further, the real endoscopic image $I_{RE}$, the detected position $PS_E$ of the endoscope, the posture $DS_E$ of the endoscope, an endoscope position $P_E$, a center line of sight vector of endoscope $VL_E$, an angle of view $A_E$ of the endoscope, a view point $VP_{VE}$ of the virtual endoscope, a center line of sight vector $VL_{VE}$ of the virtual endoscope, an angle of view $A_{VE}$ of the virtual endoscope, a 3D medical image V, a position of interest $P_I$ and a virtual endoscopic image $I_{VE}$ in the dashed line frame are data written in and read from predetermined memory areas of the image processing workstation 9 by the individual processing units in the dashed line frame.

Next, using the flow chart shown in FIG. 3, a schematic flow of operations by the user performed on the endoscopic observation support system and operations performed by the above-mentioned individual processing units according to the first embodiment of the invention is described.

Prior to observation of the interior of the abdominal cavity of a subject using the endoscope 1, the 3D medical image forming unit 5 images the interior of the abdominal cavity of the subject to form the 3D medical image V. On the image processing workstation 9, the 3D medical image obtaining unit 23 obtains the 3D medical image V formed by the 3D medical image forming unit 5 (#1), and then the position of interest identifying unit 24 shows a user interface for receiving a user operation to specify a structure of interest (for example, a site of surgical interest) in the body cavity shown in the 3D medical image V obtained by the 3D medical image obtaining unit 23, and identifies the position $P_I$ of the specified structure of interest in the 3D medical image V based on the obtained 3D medical image V (#2).

Then, as written on the right side of the flow chart shown in FIG. 3, during endoscopic surgery of the structure of interest, i.e., during observation of the interior of the abdominal cavity of the subject using the endoscope 1, the real endoscopic image forming unit 2 repeatedly forms the real endoscopic image $I_{RE}$ taken with the endoscope 1 inserted in the body cavity at a predetermined frame rate, and the formed real endoscopic image $I_{RE}$ is displayed real-time as a live-view image on the real endoscopic image display 4 until the observation is finished (#7: YES). Further, the endoscope position and posture detecting unit 11 repeatedly detects the real-time position $PS_E$ and the real-time posture $DS_E$ of the endoscope 1 inserted in the body cavity at predetermined time intervals.

On the image processing workstation 9, the real endoscopic image obtaining unit 21 obtains the real endoscopic image $I_{RE}$ formed by the real endoscopic image forming unit 2 (#3). Almost at the same time with this, the endoscope position and posture obtaining unit 22 obtains the detected endoscope position $PS_E$ and the posture $DS_E$ detected by the endoscope position and posture detecting unit 11 and outputs the endoscope position $P_E$ and the posture (center line of sight vector) $VL_E$, which are obtained by transforming the obtained endoscope position $PS_E$ and the posture $DS_E$ into a position and a posture in the coordinate system of the 3D medical image V (#4).

The endoscope angle of view obtaining unit 25 obtains the angle of view $A_E$ of the endoscope 1 from a predetermined memory area of the image processing workstation 9 (#5).

The virtual field of view determining unit 26 determines a virtual field of view of the virtual endoscope positioned at the endoscope position $P_E$ obtained by the endoscope position and posture obtaining unit 22, based on the position of structure of interest $P_I$ identified by the position of interest identifying unit 24, the position $P_E$ and the center line of sight vector $VL_E$ obtained by the endoscope position and posture obtaining unit 22, and the angle of view $A_E$ of the endoscope obtained by the endoscope angle of view obtaining unit 25, such that the position of structure of interest $P_I$ is contained within the virtual field of view and the virtual field of view has continuity with an endoscope-corresponding field of view, which is a field of view of the 3D medical image corresponding to the field of view of the endoscope 1, and outputs a view point $VP_{VE}$, the center line of sight vector $VL_{VE}$ and the angle of view $A_{VE}$ of the virtual endoscope (#6).

The virtual endoscopic image generating unit 27 generates, from the 3D medical image V obtained by the 3D medical image obtaining unit 23 and inputted thereto, the virtual endoscopic image $I_{VE}$ having the virtual field of view with the view point thereof being an endoscope-corresponding position $VP_{VE}$, based on the view point $VP_{VE}$, the center line of sight vector $VL_{VE}$ and the angle of view $A_{VE}$ of the virtual endoscope determined by the virtual field of view determining unit 26 (#7).

The display control unit 28 causes the WS display 10 to display the real endoscopic image $I_{RE}$ obtained by the real endoscopic image obtaining unit 21 and the virtual endoscopic image $I_{VE}$ generated by the virtual endoscopic image generating unit 27 (#8).

On the image processing workstation 9, operations to obtain a new real endoscopic image $I_{RE}$ (#3), to obtain the endoscope position $P_E$ and the posture $VL_{VE}$ at that point of time (#4), to obtain the angle of view $A_E$ of the endoscope (#5), to determine the virtual field of view (#6), to generate the virtual endoscopic image $I_{VE}$ (#7) and to update the real endoscopic image $I_{RE}$ and the virtual endoscopic image $I_{VE}$ being displayed (#8) are repeated until an operation to instruct to end the observation is made (#8: No). With this, the real endoscopic image $I_{RE}$ and the virtual endoscopic image $I_{VE}$ are continuously displayed on the WS display 10 in a temporally synchronized manner. When the operation to instruct to end the observation is made (#9: Yes), the image processing workstation 9 ends the repeated operations in steps #3 to #8 described above.

Next, details of the operations performed by the individual processing units in the image processing workstation 9 are described.

The real endoscopic image obtaining unit 21 is a communication interface that receives the real endoscopic image $I_{RE}$ via communication with the real endoscopic image forming unit (digital processor) 2 and stores the real endoscopic image $I_{RE}$ in a predetermined memory area of the image processing workstation 9. The real endoscopic image $I_{RE}$ is transferred from the real endoscopic image forming unit 2 based on a request from the real endoscopic image obtaining unit 21.

The endoscope position and posture obtaining unit 22 has a function of a communication interface to obtain the endoscope position $PS_E$ and the posture $DS_E$ via communication with the endoscope position and posture detecting unit 11, and a function of transforming the obtained endoscope position $PS_E$ and the posture $DS_E$ in the three-dimensional coordinate system of the position sensor 8 into the endoscope position $P_E$ and the posture (center line of sight vector) $VL_E$ represented by coordinate values in the three-dimensional coordinate system of the 3D medical image V and storing the endoscope position $P_E$ and the posture (center line of sight vector) $VL_E$ in a predetermined memory area of the image processing workstation 9. With respect to the former communication interface function, the endoscope position $PS_E$ and the posture $DS_E$ are obtained from the endoscope position detecting unit 11 based on a request from the endoscope position obtaining unit 22. With respect to the latter coordinate transformation function, an amount of rotation of coordinate axes is calculated in advance based on a correspondence relationship between the orientation of each coordinate axis in the three-dimensional coordinate system of the position sensor and the orientation of each coordinate axis in the three-dimensional coordinate system of the 3D medical image V, and coordinate values of a position on the subject corresponding to the origin of the 3D medical image V in the three-dimensional coordinate system of the position sensor 8 are measured in advance to calculate an amount of translation between the coordinate axes based on the coordinate values of the origin. Then, the transformation of the endoscope position $PS_E$ and the posture $DS_E$ represented by the three-dimensional coordinate system of the position sensor 8 into the endoscope position $P_E$ and the posture (center line of sight vector) $VL_E$ represented by the coordinate values in the three-dimensional coordinate system of the 3D medical image V is achieved using a matrix that applies rotation by the calculated amount of rotation and translation by the calculated amount of translation.

The 3D medical image obtaining unit 23 has a function of a communication interface to receive the 3D medical image V from the 3D medical image forming unit 5 and store the 3D medical image V in a predetermined memory area of the image processing workstation 9.

The position of interest identifying unit 24 shows, on a cross-sectional image representing a predetermined cross-section generated from the 3D medical image V using the known MPR method, a user interface for receiving an operation to specify the structure of interest via the pointing device or keyboard of the image processing workstation 9. For example, when the pointing device is clicked on the structure of interest shown in the cross-sectional image, the position of interest identifying unit 24 identifies the position $P_I$ of the structure of interest, which has been specified by the click, in the 3D medical image V, and stores the position $P_I$ in a predetermined memory area of the image processing workstation 9. As the structure of interest, a site of surgical interest or a site that requires attention during surgery may be specified, as desired by the user.

The endoscope angle of view obtaining unit 25 obtains information of the angle of view $A_E$ of the endoscope 1, which is set in advance in a startup parameter, a configuration file, or the like, of the program based on the specifications of the endoscope 1. In a case where the information of the angle of view $A_E$ of the endoscope 1 is added as accompanying information to the real endoscopic image $I_{RE}$, the endoscope angle of view obtaining unit 25 may obtain the information of the angle of view $A_E$ of the endoscope 1 by analyzing the accompanying information.

The virtual field of view determining unit 26 first aligns view point positions and the orientation of the center line of sight vectors of the virtual endoscope and the endoscope 1 with each other, as schematically shown in FIG. 4A. Namely, the virtual field of view determining unit 26 determines the view point position $VP_{VE}$ of the virtual endoscope to be the same as the endoscope position $P_E$ obtained by the endoscope position and posture obtaining unit 22, and determines the center line of sight vector $VL_{VE}$ of the virtual endoscope to be the same as the center line of sight vector $VL_E$ of the endoscope 1 obtained by the endoscope position and posture obtaining unit 22. Further, the virtual field of view determining unit 26 determines the angle of view $A_{VE}$ of the virtual endoscope to be wider than the angle of view $A_E$ of the endoscope 1 and such that the position of structure of interest $P_I$ is contained within the field of view of the virtual endoscope. Specifically, for example, assuming that an angle θ is formed between the center line of sight vector $VL_{VE}$ of the virtual endoscope and a vector connecting the view point position $VP_{VE}$ of the virtual endoscope and the position of structure of interest $P_I$, the angle of view $A_{VE}$ of the virtual endoscope may be found by adding a constant to larger one of the values of the angle of view $A_E$ of the endoscope 1 and 20, or by multiplying the larger one of the values by a predetermined factor larger than 1. If the value of the thus found angle of view $A_{VE}$ is larger than a predetermined threshold, this may be handled as an angle of view setting error and predetermined error processing (such as displaying a warning message, or the like, which prompts to discontinue the process, change the posture of the endoscope 1, correct the position of structure of interest $P_I$, etc.) may be carried out. The thus determined view point position $VP_{VE}$, the center line of sight vector $VL_{VE}$ and the angle of view $A_{VE}$ of the virtual endoscope are written in a predetermined memory area.

The virtual endoscopic image generating unit 27 generates the virtual endoscopic image $I_{VE}$ from the 3D medical image V inputted thereto by using the orientation of the center line of sight vector $VL_{VE}$ of the virtual endoscope as the orientation of a line of sight vector passing through the center of the field of view, as shown in FIG. 4A, to set a plurality of lines of sight radiating from the view point position $VP_{VE}$ of the virtual endoscope within the range of the angle of view $A_{VE}$, and projecting pixel values along each line of sight by volume rendering using the known center perspective projection. For the volume rendering, a color template is used, which defines the color and the transparency in advance such that an image showing the sites in the abdominal cavity in almost the same appearance as those shown in the real endoscopic image $I_{RE}$ is obtained.

The display control unit 28 generates a display screen where the real endoscopic image $I_{RE}$ and the virtual endoscopic image $I_{VE}$ are superimposed one on the other with aligning the centers of the fields of view of the images to align corresponding positions thereof with each other, and outputs the generated screen to the WS display 10. In this manner, the display screen where the real endoscopic image $I_{RE}$ and the virtual endoscopic image $I_{VE}$ are superimposed one on the other, as schematically shown in FIG. 4B as an example, is displayed on the WS display 10. The superposition of the images may be achieved, for example, by the known alpha blending.

As described above, according to the first embodiment of the invention, the virtual field of view determining unit 26 uses the endoscope position $P_E$ obtained by the endoscope position and posture obtaining unit 22 as the view point position $VP_{VE}$ of the virtual endoscope, uses the center line of sight vector $VL_E$ of the endoscope 1 obtained by the endoscope position and posture obtaining unit 22 as the center line of sight vector $VL_{VE}$ of the virtual endoscope, and determines the angle of view $A_{VE}$ of the virtual endoscope to be wider than the angle of view $A_E$ of the endoscope 1 and such that the position of structure of interest $P_I$ is contained within the field of view of the virtual endoscope, thereby making the position of structure of interest $P_I$ be contained within the virtual field of view and the virtual field of view have continuity with the endoscope-corresponding field of view, which is a field of view corresponding to the field of view of the endoscope 1 in the 3D medical image. The virtual endoscopic image generating unit 27 generates, from the 3D medical image V obtained by the 3D medical image obtaining unit 23 and inputted thereto, the virtual endoscopic image $I_{VE}$ having the above-described virtual field of view with the view point thereof being the endoscope-corresponding position $VP_{VE}$, based on the view point $VP_{VE}$, the center line of sight vector $VL_{VE}$ and the angle of view $A_{VE}$ of the virtual endoscope determined by the virtual field of view determining unit 26, and the display control unit 28 causes the WS display 10 to display the real endoscopic image $I_{RE}$ and the virtual endoscopic image $I_{VE}$ superimposed one on the other. The displayed virtual endoscopic image $I_{VE}$ always contains the position of structure of interest $P_I$, thereby allowing the user to reliably recognize the positional relationship and the approach between the endoscope 1 and the structure of interest, and thus helping to prevent misoperation, etc., during surgery or examination. Further, as shown in FIG. 4B as an example, the field of view of the virtual endoscopic image $I_{VE}$ contains the field of view of the endoscope 1. This facilitates the user to recognize the positional relationship between these fields of view, and even when the structure of interest is not contained in the real endoscopic image $I_{RE}$, for example, the user can easily tell how the endoscope 1 should be moved to capture the structure of interest in the field of view of the real endoscope 1 by checking the position of the structure of interest in the virtual endoscopic image $I_{VE}$, and this serves to improve operability of the endoscope 1 during surgery.

Further, at this time, the field of view of the virtual endoscope of the continuously displayed virtual endoscopic image $I_{VE}$ is changed real-time by feedback of the real-time position of the endoscope 1 detected by the endoscope position and posture detecting unit 11. This allows the user to dynamically and more appropriately recognize the approach of the endoscope 1 to the structure of interest.

Further, the real endoscopic image forming unit 2 forms the real endoscopic image $I_{RE}$ which represents the interior of the body cavity taken real-time with the endoscope 1, and the real endoscopic image $I_{RE}$ which is formed almost at the same time when the position of the endoscope 1 used to generate the virtual endoscopic image $I_{VE}$ is detected is displayed with being superimposed on the virtual endoscopic image $I_{VE}$. The real endoscopic image $I_{RE}$ and the virtual endoscopic image $I_{VE}$ show the state of the interior of the body cavity almost at the same point of time, and thus the real endoscopic image $I_{RE}$ and the virtual endoscopic image $I_{VE}$ are continuously displayed with being superimposed one on the other in a temporally synchronized manner. Further, at this time, the field of view of the real endoscopic image $I_{RE}$ and the field of view of the virtual endoscopic image $I_{VE}$ change along with movement or rotation of the endoscope 1. In this manner, in the first embodiment of the invention, the user can observe the interior of the body cavity real-time with complementarily using the real endoscopic image $I_{RE}$ and the virtual endoscopic image $I_{VE}$.

Still further, the virtual endoscopic image generating unit 27 generates the virtual endoscopic image $I_{VE}$ using the color template, which defines color and transparency in advance such that an image showing the sites in the abdominal cavity in almost the same appearance as those shown in the real endoscopic image $I_{RE}$ is obtained. Therefore, the user can observe both the real endoscopic image $I_{RE}$ and the virtual endoscopic image $I_{VE}$, which are displayed on the WS display 10 by the display control unit 28 with being superimposed one on the other, without a feel of inconsistency.

Although the display control unit 28 causes the real endoscopic image $I_{RE}$ and the virtual endoscopic image $I_{VE}$ to be displayed with being superimposed one on the other in the above-described embodiment, the real endoscopic image $I_{RE}$ and the virtual endoscopic image $I_{VE}$ may be displayed side by side.

Further, in the above-described embodiment, the virtual field of view determining unit 26 makes the position of structure of interest $P_I$ be contained within the virtual field of view by setting only the angle of view $A_{VE}$ of the virtual endoscope different from the angle of view of the endoscope 1. However, as a modification of setting of the field of view of the virtual endoscope, the center line of sight vector $VL_{VE}$ of the virtual endoscope which is different from the center line of sight vector $VL_E$ of the endoscope 1 may be set to make the position of structure of interest $P_I$ be contained within the virtual field of view.

Figures 7A, 7B:
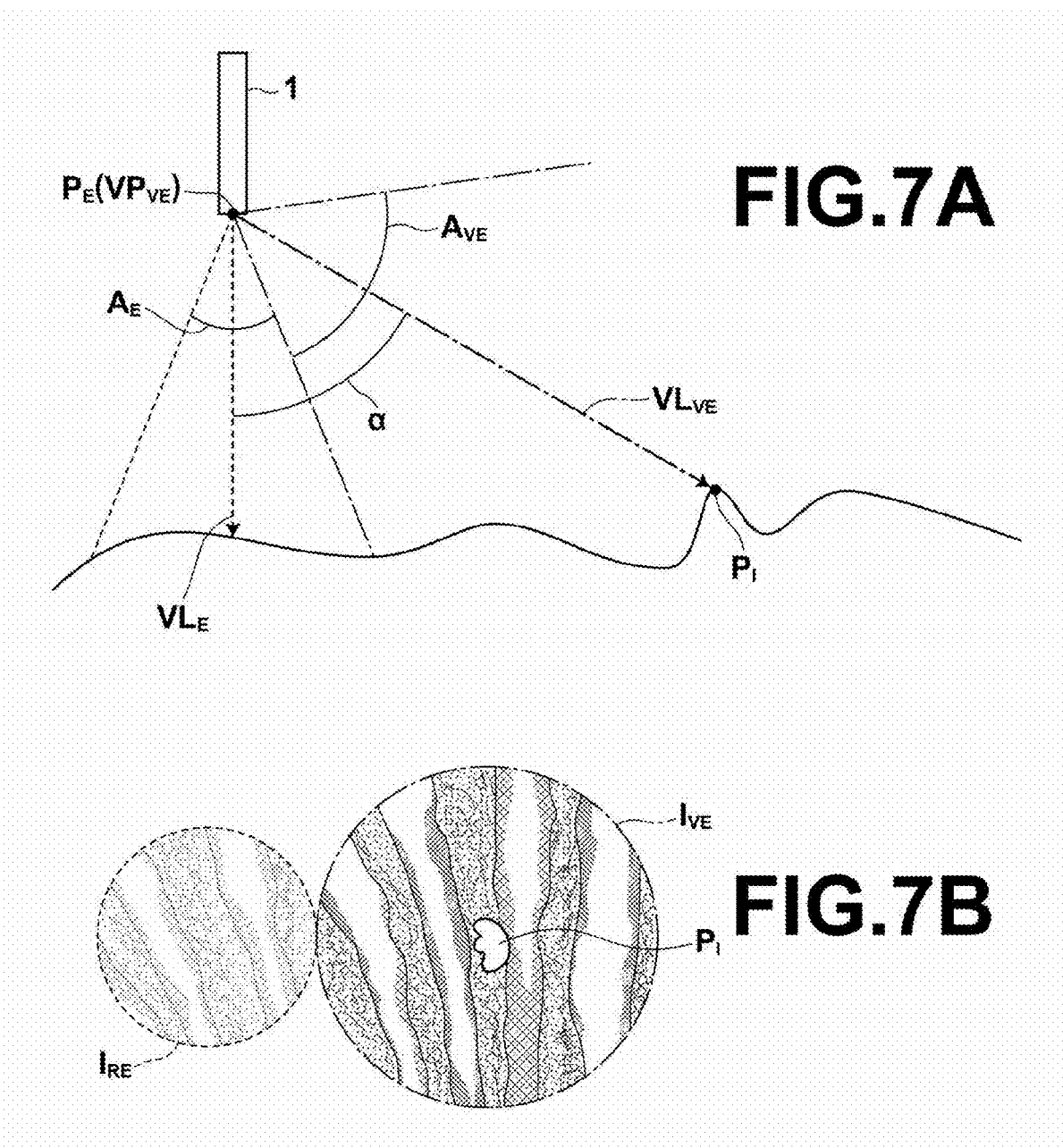
FIG. 7A is a diagram schematically illustrating a third example of the field of view of the virtual endoscope, which is determined based on the field of view of the real endoscope and the position of the structure of interest, in the modification of the first embodiment of the invention.
FIG. 7B is a diagram schematically illustrating one example of the superimposed display of the real endoscopic image and the virtual endoscopic image in the case shown in FIG. 7A in the modification of the first embodiment of the invention.

Each of FIGS. 5A, 6A and 7A shows, for each positional relationship between the view point $VP_{VE}$ ($VP_E$) and the position of the structure of interest, an example of the center line of sight vector $VL_{VE}$ that is set to make the position of structure of interest $P_I$ be the center of the virtual field of view. In these examples, the virtual field of view determining unit 26 determines the orientation of the center line of sight vector $VL_{VE}$ of the virtual endoscope such that the vector $VL_{VE}$ connects the view point $VP_{VE}$ ($VP_E$) and the position of structure of interest $P_I$, and determines the angle of view $A_{VE}$ of the virtual endoscope to be wider than the angle of view $A_E$ of the endoscope 1 and have continuity with the field of view of the endoscope 1. Specifically, assuming that an angle α is formed between the center line of sight vector $VL_E$ of the endoscope 1 and the center line of sight vector $VL_{VE}$ of the virtual endoscope, the field of view of the virtual endoscope having continuity with the field of view of the endoscope 1 satisfies Equation (1) below:

$$\alpha - A_E/2 \leq A_{VE}/2 \tag{1}$$

Further, assuming that the angle of view of virtual endoscope has an initial value $A_{VE0}$ (where $A_{VE0} > A_E$) defined in advance, the angle of view $A_{VE}$ of the virtual endoscope wider than the angle of view $A_E$ of the endoscope 1 takes larger one of the initial value $A_{VE0}$ and ($2\alpha - A_E$). It should be noted that a constant may further be added to $2\alpha - A_E$, or $2\alpha - A_E$ may be multiplied with a predetermined factor larger than 1.

FIG. 5A shows a case where the position of structure of interest $P_I$ is contained in the field of view of the endoscope 1, i.e., where $\alpha < A_E/2$. In this case, the angle of view $A_{VE}$ of the virtual endoscope is determined to be the initial value $A_{VE0}$, and the field of view of the real endoscopic image $I_{RE}$ is contained within the field of view of the virtual endoscopic image $I_{VE}$, as shown in FIG. 5B. It should be noted that, depending on the value of the initial value $A_{VE0}$, the field of view of the real endoscopic image $I_{RE}$ and the field of view of the virtual endoscopic image $I_{VE}$ may overlap with each other. In contrast, as shown in FIG. 6A, in a case where the distance between the position of the structure of interest and the center of the field of view of the endoscope 1 is somewhat larger, more precisely, where $0 < \alpha - A_E/2 < A_{VE0}/2$, the angle of view $A_{VE}$ of the virtual endoscope is determined to be the initial value $A_{VE0}$, and the field of view of the real endoscopic image $I_{RE}$ and the field of view of the virtual endoscopic image $I_{VE}$ partially overlap with each other, as shown in FIG. 6B. Further, as shown in FIG. 7A, in a case where the distance between the position of structure of interest $P_I$ and the center of the field of view of the endoscope 1 is even larger, more precisely, where $0 < A_{VE0}/2 < \alpha - A_E/2$, the angle of view $A_{VE}$ of the virtual endoscope is determined to be $\alpha - A_E/2$, and the field of view of the real endoscopic image $I_{RE}$ contacts the field of view of the virtual endoscopic image $I_{VE}$ only at a single point, as shown in FIG. 7B.

Alternatively, the virtual field of view determining unit 26 may determine the center line of sight vector $VL_{VE}$ of the virtual endoscope to be a line of sight that divides the angle $\alpha$ into equal halves, and may determine the angle of view $A_{VE}$ to be a value larger than $A_{VE0}$ and $\alpha$.

Further, in these modifications of the setting of the field of view of the virtual endoscope, the display control unit 28 may align corresponding positions of the real endoscopic image $I_{RE}$ and the virtual endoscopic image $I_{VE}$ with each other by identifying a positional relationship between the endoscope 1 and the line of sight (light beam) of the virtual endoscope based on the position $P_E$ and the posture (center line of sight vector) $VL_E$ of the endoscope 1, and the view point $VP_{VE}$ ($VP_E$) and the center line of sight vector (posture) $VL_{VE}$ of the virtual endoscope, as shown in FIGS. 5A, 6A and 7A as examples, to generate a display screen where the real endoscopic image $I_{RE}$ and the virtual endoscopic image $I_{VE}$ are superimpose one on the other, as shown in each of FIGS. 5B, 6B and 7BA as examples.

It should be noted that, in these modifications of the setting of the field of view of the virtual endoscope, when the superimposed display of the real endoscopic image $I_{RE}$ and the virtual endoscopic image $I_{VE}$ is carried out, if the center of the field of view of the real endoscopic image $I_{RE}$ and the center of the field of view of the virtual endoscopic image $I_{VE}$ are not aligned with each other, the peripheral area of the real endoscopic image $I_{RE}$ is distorted by distortion aberration due to optical characteristics of the endoscope 1 (in particular, characteristics of the wide-angle lens), and this may hinder the continuity of the image at the boundary between the real endoscopic image $I_{RE}$ and the virtual endoscopic image $I_{VE}$. Therefore, the real endoscopic image $I_{RE}$ may be corrected for the distortion aberration using a function for coordinate transformation and a coordinate transformation map depending on the optical characteristics of the endoscope 1 so that the corrected real endoscopic image and the virtual endoscopic image $I_{VE}$ are preferably superimposed one on the other (see Japanese Unexamined Patent Publication No. 2009-276371, etc., for details of the distortion aberration correction). Alternatively, a function and a transformation map for transformation reverse to the distortion aberration correction may be used to carry out a correction to distort the virtual endoscopic image $I_{VE}$, so that the real endoscopic image $I_{RE}$ and the corrected virtual endoscopic image are superimposed one on the other.

Further, in the above-described embodiment, the position of interest identifying unit 24 may extract a region representing the entire structure of interest based on the position of structure of interest $P_I$ specified by the user, and the virtual endoscopic image generating unit 27 may perform volume rendering using a different color template for this region of the structure of interest from one that is used to other structures. With this, visual recognizability of the region of the structure of interest in the virtual endoscopic image $I_{VE}$ shown in FIG. 4B is improved, and this is even more effective. It should be noted that the extraction of the region of the structure of interest may be achieved using, for example, a technique disclosed in Japanese Unexamined Patent Publication No. 2008-245719 proposed by the present applicant. Specifically, setting of an arbitrary point $P_I$ in the region of the structure of interest is received (this point will hereinafter be referred to as "user set point"), and a three-dimensional range where a lesion region may be present is determined using information of a possible size of the lesion region defined in advance. Then, the lesion region is extracted based on the set point and a point outside the determined range by using a region segmentation method, such as graph cutting, for example.

A second embodiment of the invention is a modification of a volume rendering process carried out by the virtual endoscopic image generating unit 27. The hardware configuration, the functional blocks and the overall flow of the process of the endoscopic observation support system of the second embodiment are the same as those in the first embodiment.

Figures 8A, 8B:
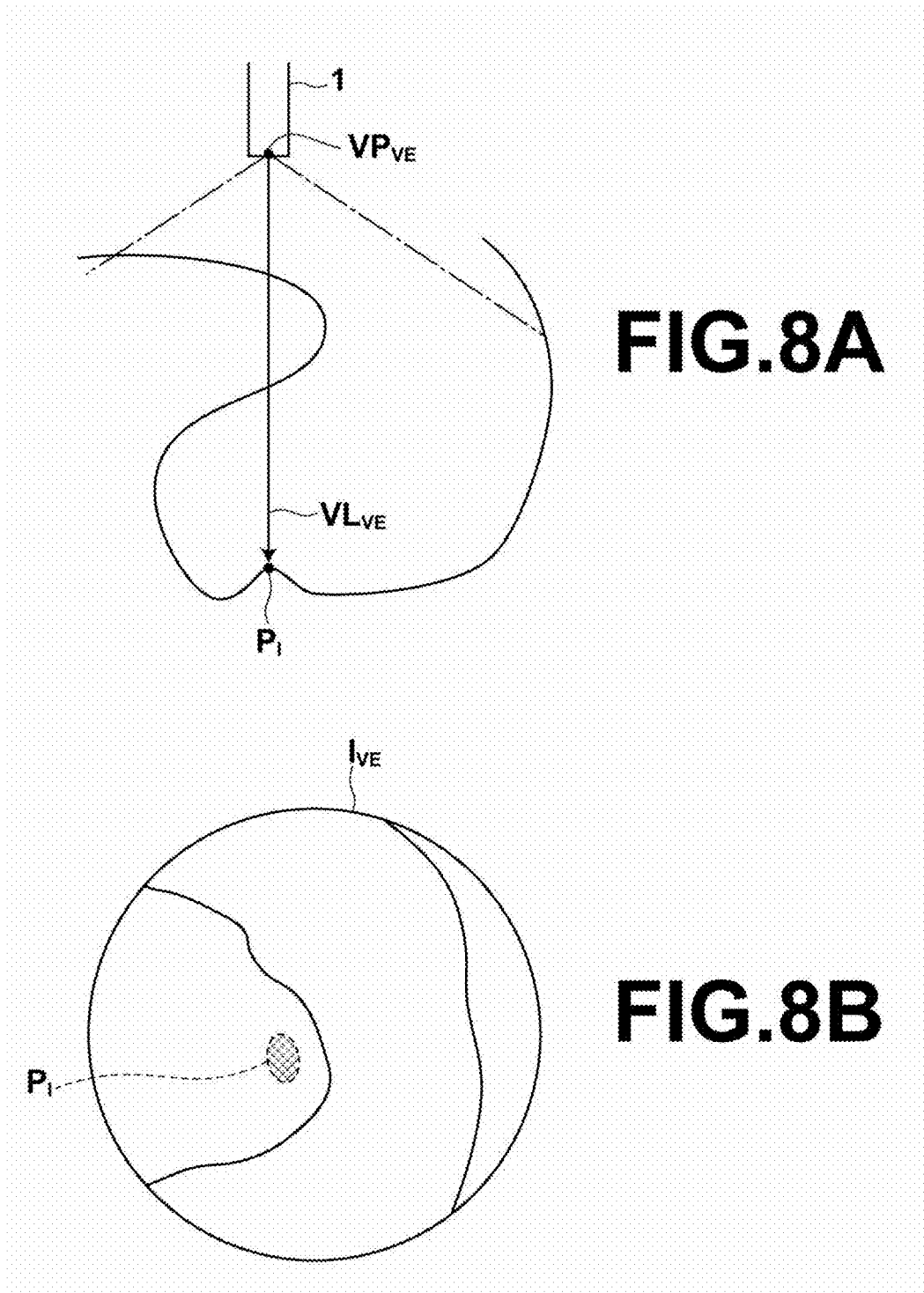
FIG. 8A is a diagram schematically illustrating one example of a case where another structure is present between the structure of interest and the endoscope.
FIG. 8B is a diagram schematically illustrating one example of the virtual endoscopic image that is displayed in the second embodiment of the invention.

FIG. 8A schematically illustrates one example of a positional relationship between the structure of interest and the endoscope 1. As shown in the drawing, in a case where there is another anatomical structure that obstructs the view between position $P_E$ of the endoscope 1, which is used as the view point of the virtual endoscopic image $I_{VE}$, and the position of the structure of interest, if the color template is defined to provide the anatomical structure with high opacity, the structure of interest behind the anatomical structure is not shown in the virtual endoscopic image $I_{VE}$. Therefore, in the second embodiment of the invention, the virtual endoscopic image generating unit 27 generates the virtual endoscopic image $I_{VE}$ using a color template that defines opacity such that the sites in the body cavity are shown semitransparent. In the thus generated virtual endoscopic image $I_{VE}$, as schematically shown in FIG. 8B, the anatomical structure present between the position $P_I$ of the structure of interest and the endoscope position $P_E$ is shown semitransparent, and a position corresponding to the position of the structure of interest $P_I$ behind the anatomical structure is shown in a visually recognizable manner. In particular, as described above as the modification of the first embodiment, in the case where the region of the structure of interest is extracted and a different color template from one that is used for other regions is used, the entire region of the structure of interest is shown in a highly visually recognizable manner even when another anatomical structure is present between the position of structure of interest $P_I$ and the endoscope position $P_E$. Such an image where an anatomical structure in the abdominal cavity is shown semitransparent cannot be formed by the real endoscopic image forming unit 2, and therefore practical value of using the virtual endoscopic image $I_{VE}$ showing such a semitransparent anatomical structure complementarily to the real endoscopic image $I_{RE}$ is very high.

A third embodiment of the invention is also a modification of the volume rendering process carried out by the virtual endoscopic image generating unit 27. The hardware configuration, the functional blocks and the overall flow of the process of the endoscopic observation support system of the third embodiment are the same as those in the first embodiment.

Figure 9A:
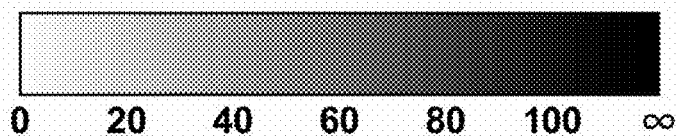
FIG. 9A is a diagram schematically illustrating one example of a color template for changing a display color in the virtual endoscopic image depending on a distance from a view point to the surface of an anatomical structure in the abdominal cavity according to the third embodiment of the invention.
Figure 9B:
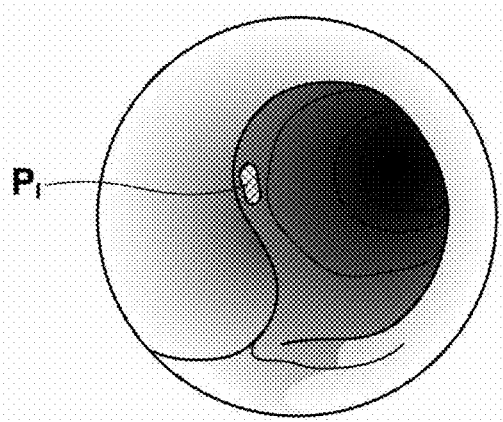
FIG. 9B is a diagram schematically illustrating one example of the virtual endoscopic image, in which the display color is changed depending on the distance from the view point, according to the third embodiment of the invention.

FIG. 9A schematically illustrates one example of the color template used in the third embodiment of the invention. As shown in the drawing, this color template is defined such that the color of the virtual endoscopic image $I_{VE}$ is changed depending on a distance from the position $P_E$ of the endoscope 1 (which is the same as the view point position PVE of the virtual endoscope) to the surface of a structure in the abdominal cavity. For example, the virtual endoscopic image generating unit 27 detects a position where a change of pixel value along each line of sight of the perspective projection is larger than a predetermined threshold or a position where the pixel value is equal to or larger than a predetermined threshold as the surface of a structure in the abdominal cavity, and calculates the distance from the position $P_E$ of the endoscope 1 to the surface of the structure in the abdominal cavity. Then, the virtual endoscopic image generating unit 27 uses the color template to determine the pixel value of the detected surface of the structure shown in the virtual endoscopic image $I_{VE}$. The thus generated virtual endoscopic image $I_{VE}$ has a thinner color at the surface of a structure nearer to the position $P_E$ of the endoscope 1, and a denser color at the surface of a structure farther from the position $P_E$ of the endoscope 1, as schematically shown in FIG. 9B as an example. In this manner, depth perception of the virtual endoscopic image $I_{VE}$, which is hard to be perceived, can be compensated for, thereby facilitating the user to recognize the approach of the endoscope 1 to the structure in the abdominal cavity (including the structure of interest).

Figure 10:
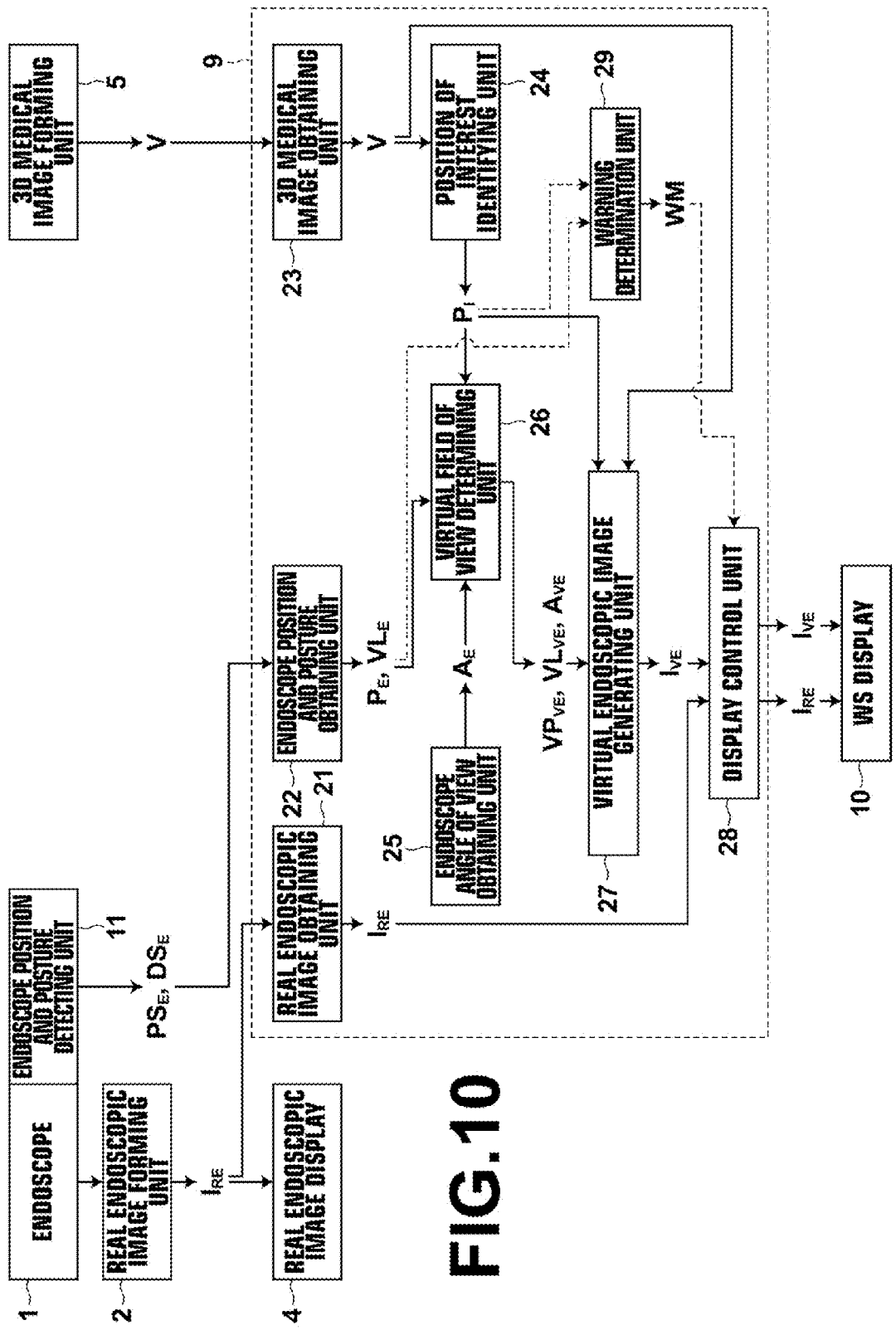
FIG. 10 is a functional block diagram of the endoscopic observation support system according to the fourth embodiment of the invention.

As shown in the functional block diagram of FIG. 10, a fourth embodiment of the invention includes a warning determination unit 29 in addition to the components of the first embodiment. The hardware configuration of the endoscopic observation support system of the fourth embodiment is the same as that in the first embodiment.

The warning determination unit 29 is a processing unit implemented on the image processing workstation 9. The warning determination unit 28 calculates a distance between the position $P_E$ of the endoscope 1 and the position $P_I$ of the structure of interest. If the calculated distance is smaller than a predetermined threshold, i.e., if the endoscope 1 approaches too close to the structure of interest, the warning determination unit 28 outputs a warning message WM.

Figure 11:
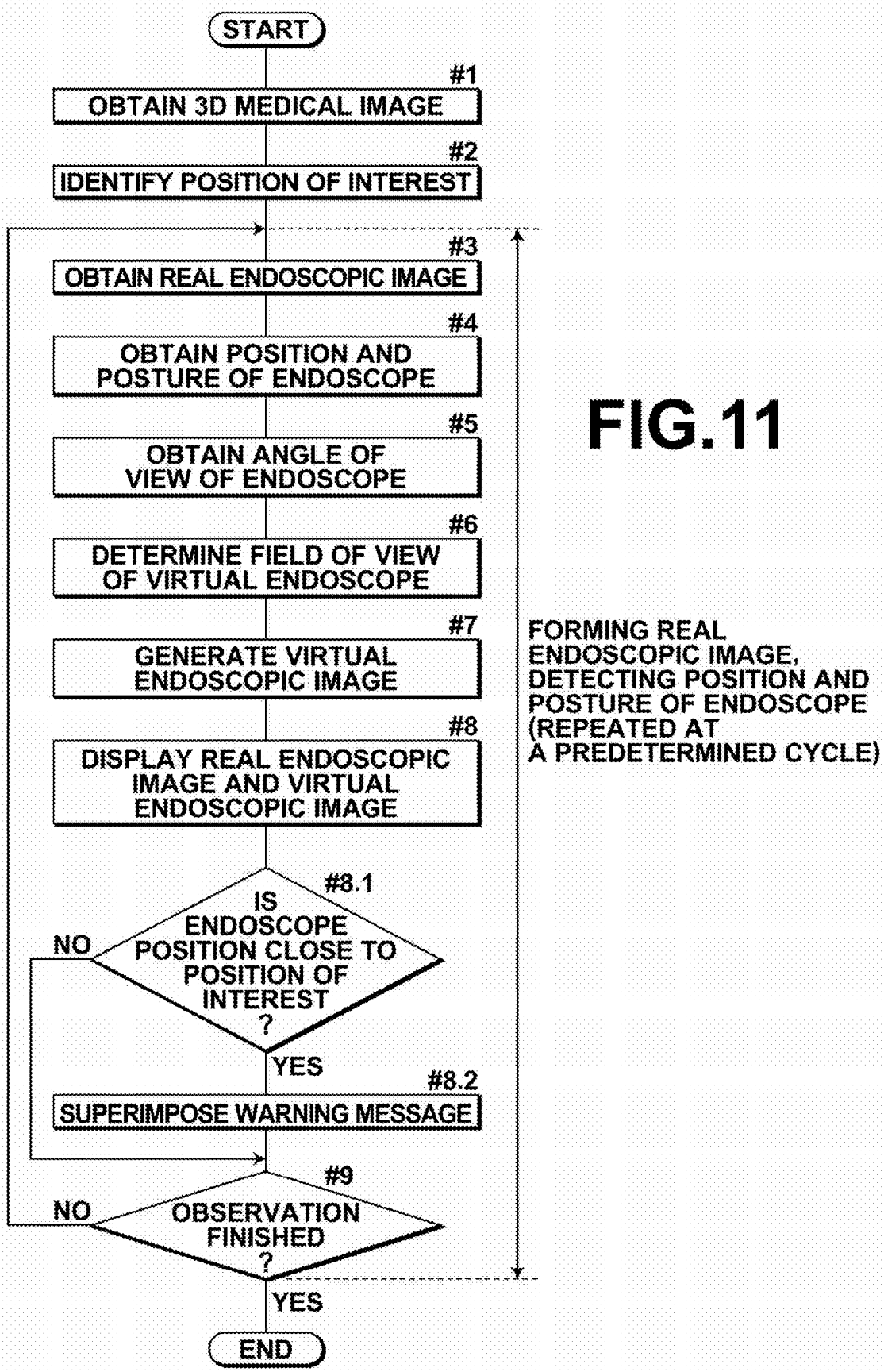
FIG. 11 is a flow chart illustrating the flow of the endoscopic observation support process according to the fourth embodiment of the invention.
Figure 12:
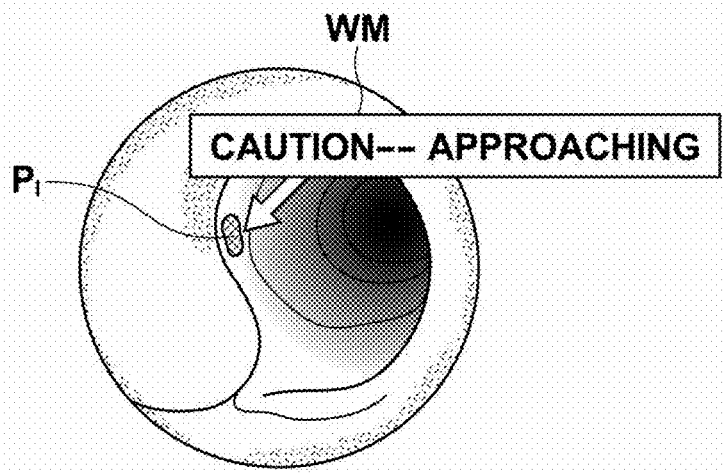
FIG. 12 is a diagram schematically illustrating one example of a warning display according to the fourth embodiment of the invention.

FIG. 11 is a flow chart illustrating the flow of the endoscopic observation support process according to the fourth embodiment of the invention. As shown in the drawing, after the real endoscopic image $I_{RE}$ and the virtual endoscopic image $I_{VE}$ are displayed in step #8 of the first embodiment, the warning determination unit 29 compares the above-described distance with the threshold (#8.1). If the distance is smaller than the threshold (#8.1:Yes), the warning determination unit 29 outputs the warning message WM, and the display control unit 28 superimposes an arrow mark with a comment "CAUTION—APPROACHING" in the vicinity of the displayed position of structure of interest $P_I$, as shown in FIG. 11 as an example. This facilitates the user to recognize the abnormal approach of the endoscope 1 to the structure of interest, thereby helping to prevent misoperation of the endoscope 1. Such a warning display is particularly effective when a blood vessel, or the like, which will cause massive bleeding if it is damaged during surgery, is specified as the structure of interest at the position of interest identifying unit 24.

Besides being superimposed on the displayed virtual endoscopic image $I_{VE}$, as described above, the warning message may be outputted in the form of a warning sound or voice, or may be outputted both as the superimposed warning message and the warning sound. Further, a risk determination table that defines a risk depending on the distance in a stepwise manner may be prepared in advance, and the warning determination unit 29 may reference the risk determination table based on the calculated distance to determine the risk, and the determined value of the risk may be outputted as the warning message WM and the display control unit 28 may display an icon, or the like, corresponding to the risk on the WS display 10.

Figure 13:
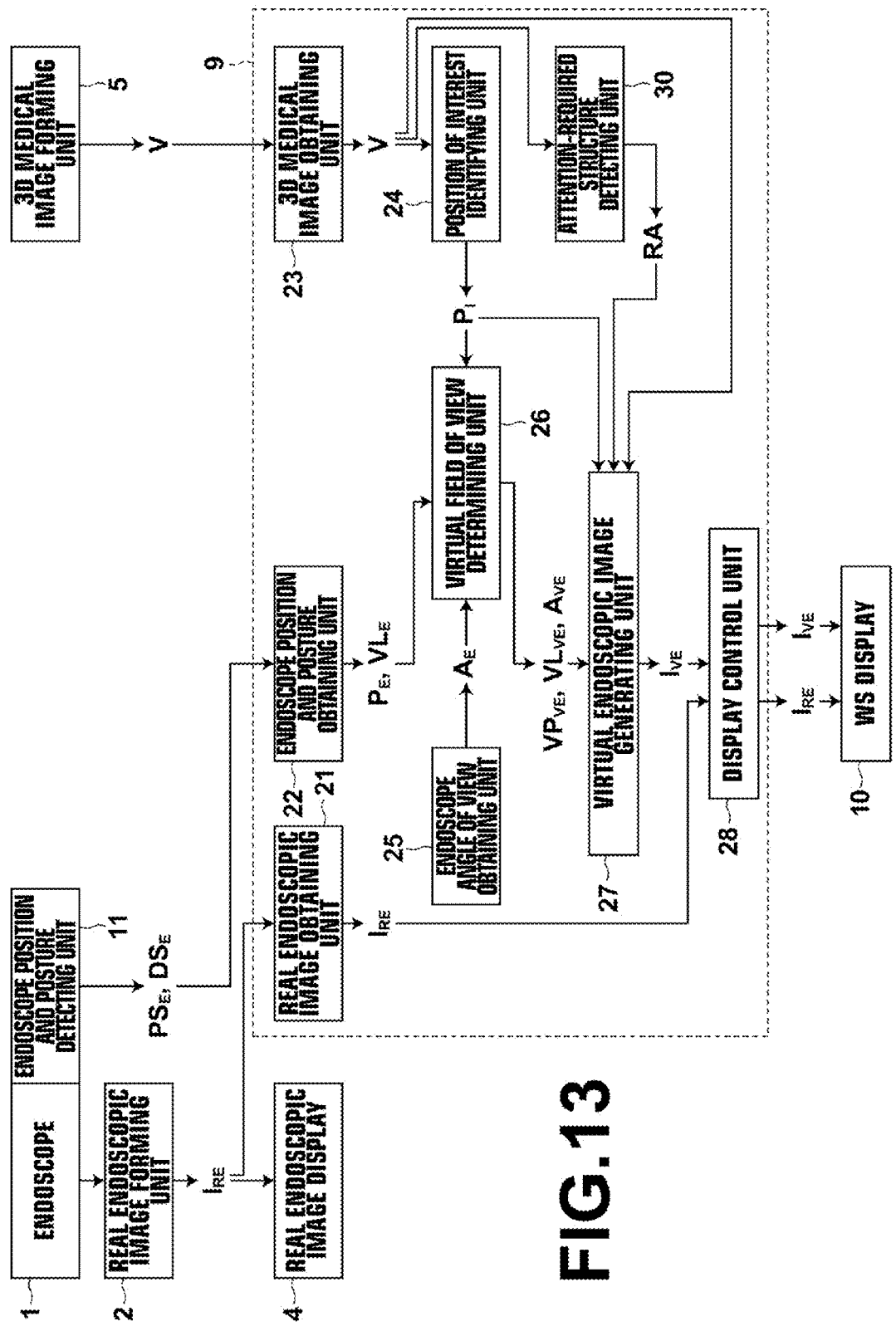
FIG. 13 is a functional block diagram of the endoscopic observation support system according to the fifth embodiment of the invention.

As shown in the functional block diagram of FIG. 13, a fifth embodiment of the invention includes an attention-required structure detecting unit 30 in addition to the components of the first embodiment. The hardware configuration of the endoscopic observation support system is the same as that of the first embodiment.

Figure 15A:
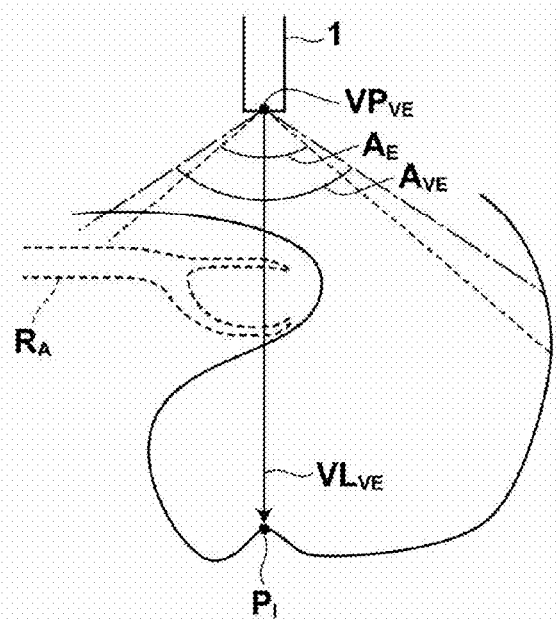
FIG. 15A is a diagram schematically illustrating one example of a positional relationship among a structure of interest, an attention-required structure and the endoscope.

The attention-required structure detecting unit 30 is a processing unit implemented on the image processing workstation 9. The attention-required structure detecting unit 30 detects a region of attention-required structure RA from the 3D medical image V inputted thereto using a known image recognition technique. FIG. 15A schematically illustrates one example of a positional relationship among the endoscope 1, the structure of interest and the attention-required structure. In this example, the attention-required structure detecting unit 30 detects an attention-required blood vessel region RA that is located behind the abdominal wall by performing known blood vessel extraction processing.

Figure 14:
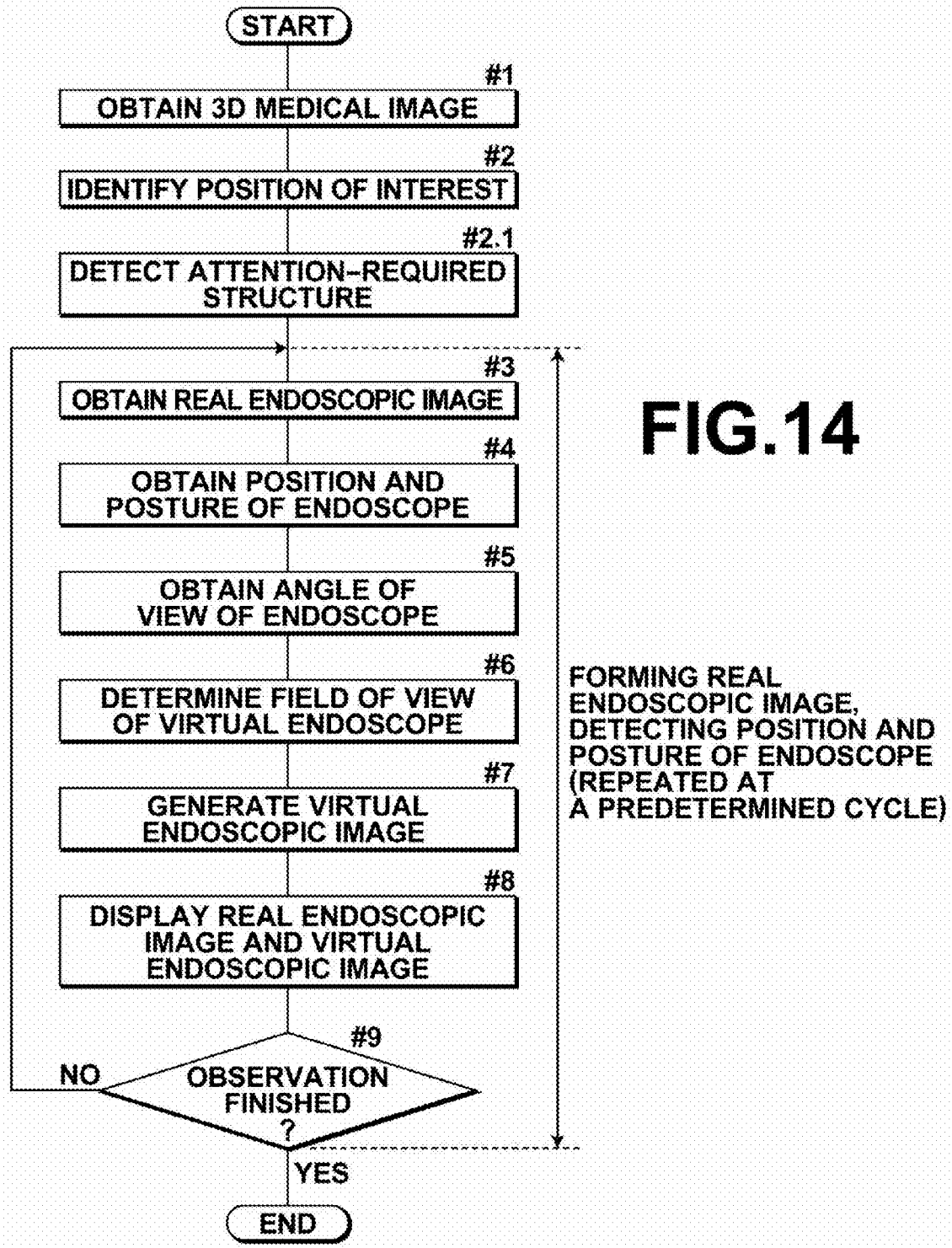
FIG. 14 is a flow chart illustrating the flow of the endoscopic observation support process according to the fifth embodiment of the invention.
Figure 15B:
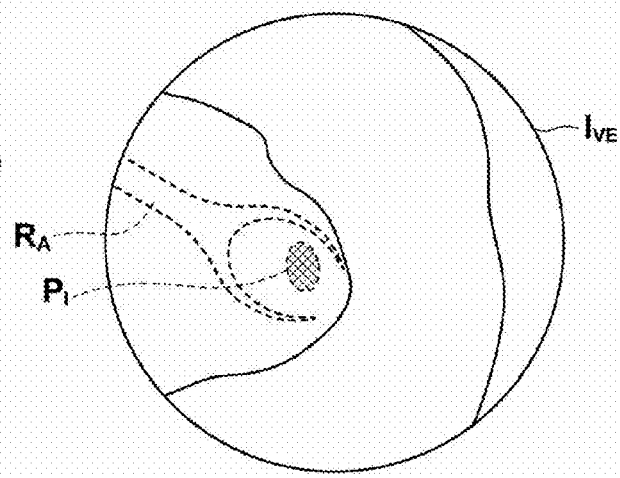
FIG. 15B is a diagram schematically illustrating one example of the virtual endoscopic image that is displayed in the fifth embodiment of the invention.

FIG. 14 is a flow chart illustrating the flow of the endoscopic observation support process according to the fifth embodiment of the invention. As shown in the drawing, after the position of interest $P_I$ is identified in step #2 of the first embodiment, the attention-required structure detecting unit 30 detects the region of attention-required structure RA (#2.1). In step #7, the virtual endoscopic image generating unit 27 generates the virtual endoscopic image $I_{VE}$ using a color template that is defined to show the region of attention-required structure RA in a visually recognizable manner. FIG. 15B schematically illustrates one example of the generated virtual endoscopic image $I_{VE}$. The virtual endoscopic image $I_{VE}$ shown in the drawing is generated using a color template that defines color and opacity such that pixels representing the abdominal wall are shown semitransparent to increase the visual recognizability of pixels representing the blood vessel. This increases the visual recognizability of the attention-required structure, thereby helping to prevent misoperation of the endoscope 1 and the surgical tool 6, similarly to the fourth embodiment.

Figure 15C:
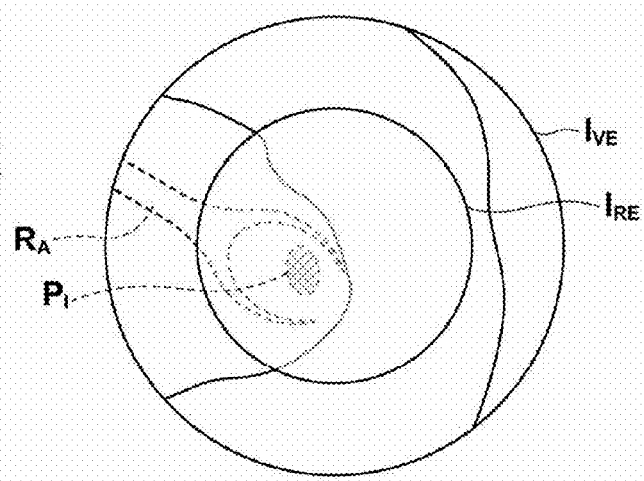
FIG. 15C is a diagram schematically illustrating one example of the superimposed display of the real endoscopic image and the virtual endoscopic image in the fifth embodiment of the invention.

FIG. 15C schematically shows a case where the generated virtual endoscopic image $I_{VE}$ and the real endoscopic image $I_{RE}$ are displayed with being superimposed one on the other with aligning the corresponding positions thereof with each other. As shown in the drawing, the attention-required structure region RA detected by the attention-required structure detecting unit 30 may also be superimposed on the real endoscopic image $I_{RE}$ to allow the user to recognize the attention-required structure in the real endoscopic image $I_{RE}$.

It should be noted that the attention-required structure detecting unit 30 may detect the region of attention-required structure RA via manual operation by the user. Further, a marker, such as an arrow, and an annotation, such as a text comment, may be superimposed on the region of attention-required structure RA.

Figure 16:
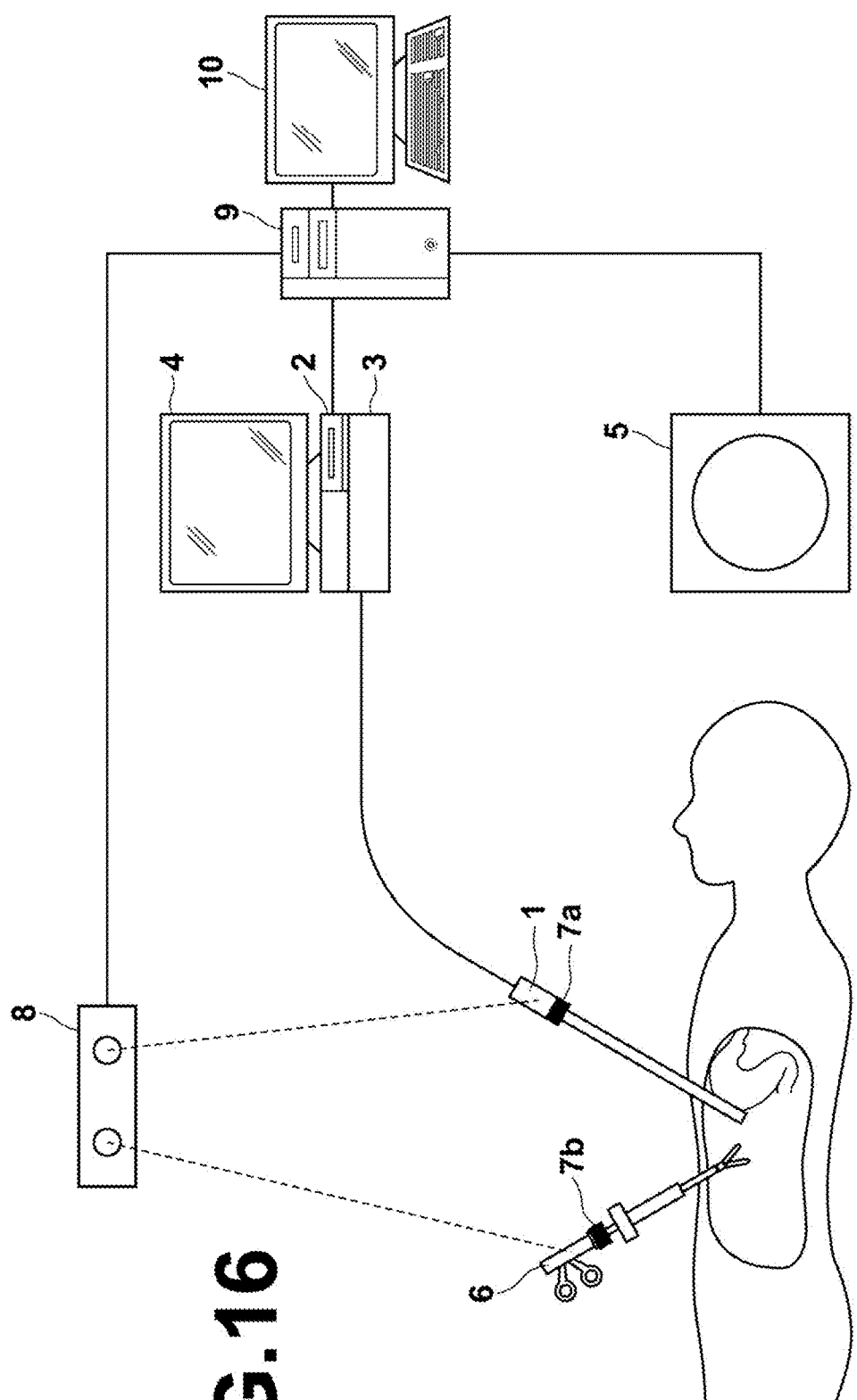
FIG. 16 is a diagram illustrating the hardware configuration of the endoscopic observation support system according to a sixth embodiment of the invention.

In a sixth embodiment of the invention, a virtual endoscopic image containing both the structure of interest and a surgical tool in the field of view thereof is generated. As can be seen from the hardware configuration shown in FIG. 16, the sixth embodiment includes a surgical tool marker 7b in addition to the hardware configuration of the first embodiment shown in FIG. 1.

Similarly to the endoscope marker 7a, the surgical tool marker 7b forms a three-dimensional position measurement system together with the position sensor 8. The surgical tool marker 7b is provided in the vicinity of handle of the surgical tool 6, and a three-dimensional position of the marker 7b is detected by the position sensor 8 at predetermined time intervals. A three-dimensional position $PS_T$ of the tip portion of the surgical tool 6 may be calculated by an offset calculation.

Figure 17:
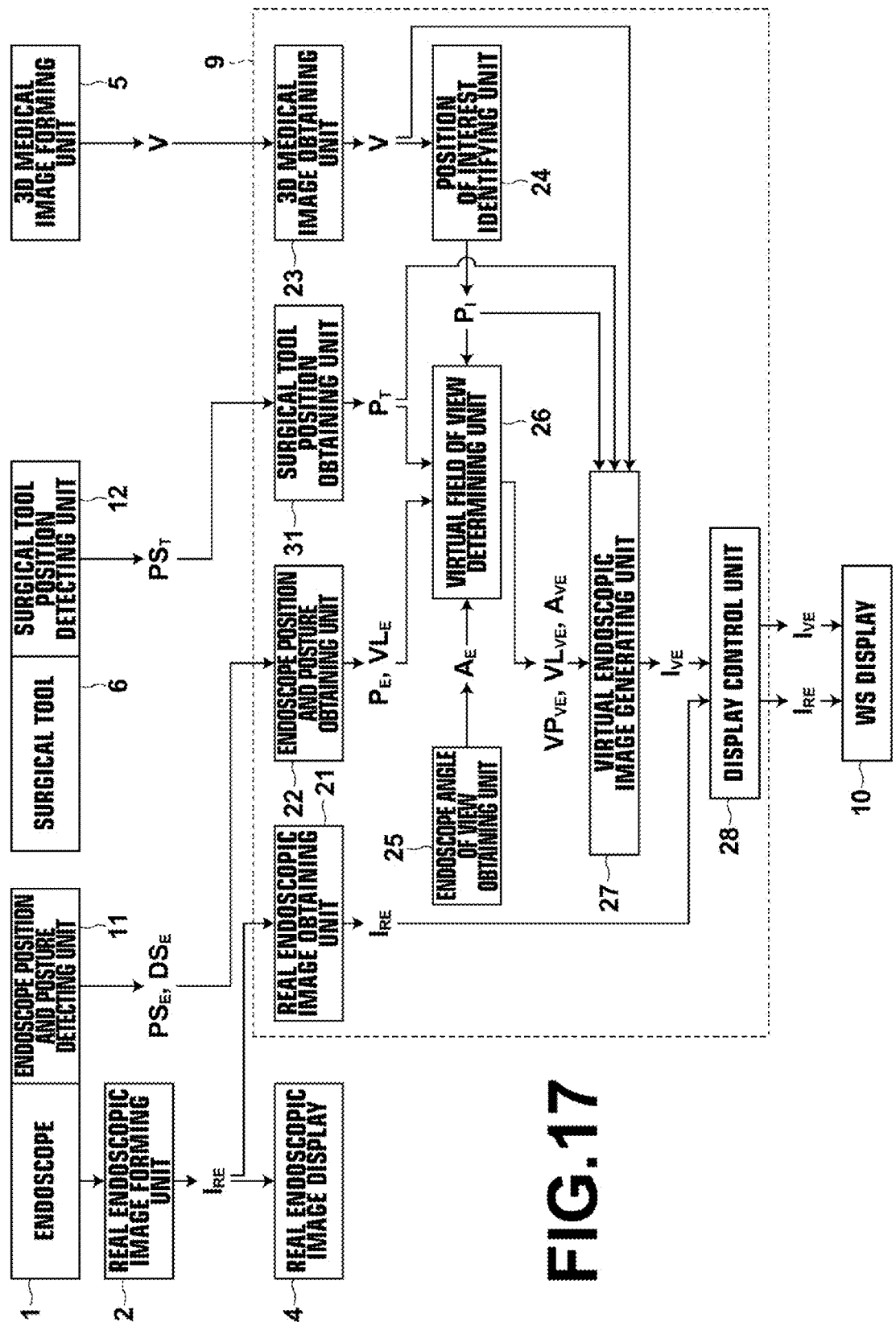
FIG. 17 is a functional block diagram of the endoscopic observation support system according to a sixth embodiment of the invention.

FIG. 17 is a functional block diagram of the sixth embodiment of the invention. The sixth embodiment includes the surgical tool 6, a surgical tool position detecting unit 12 and a surgical tool position obtaining unit 31 in addition to the configuration of the first embodiment shown in FIG. 2. The function of the surgical tool position detecting unit 12 is implemented by the surgical tool marker 7b and the position sensor 8 shown in FIG. 16. The surgical tool position $P_T$ is data written in and read from a predetermined memory area of the image processing workstation 9 by the individual processing units shown in the dashed line frame.

Figure 18:
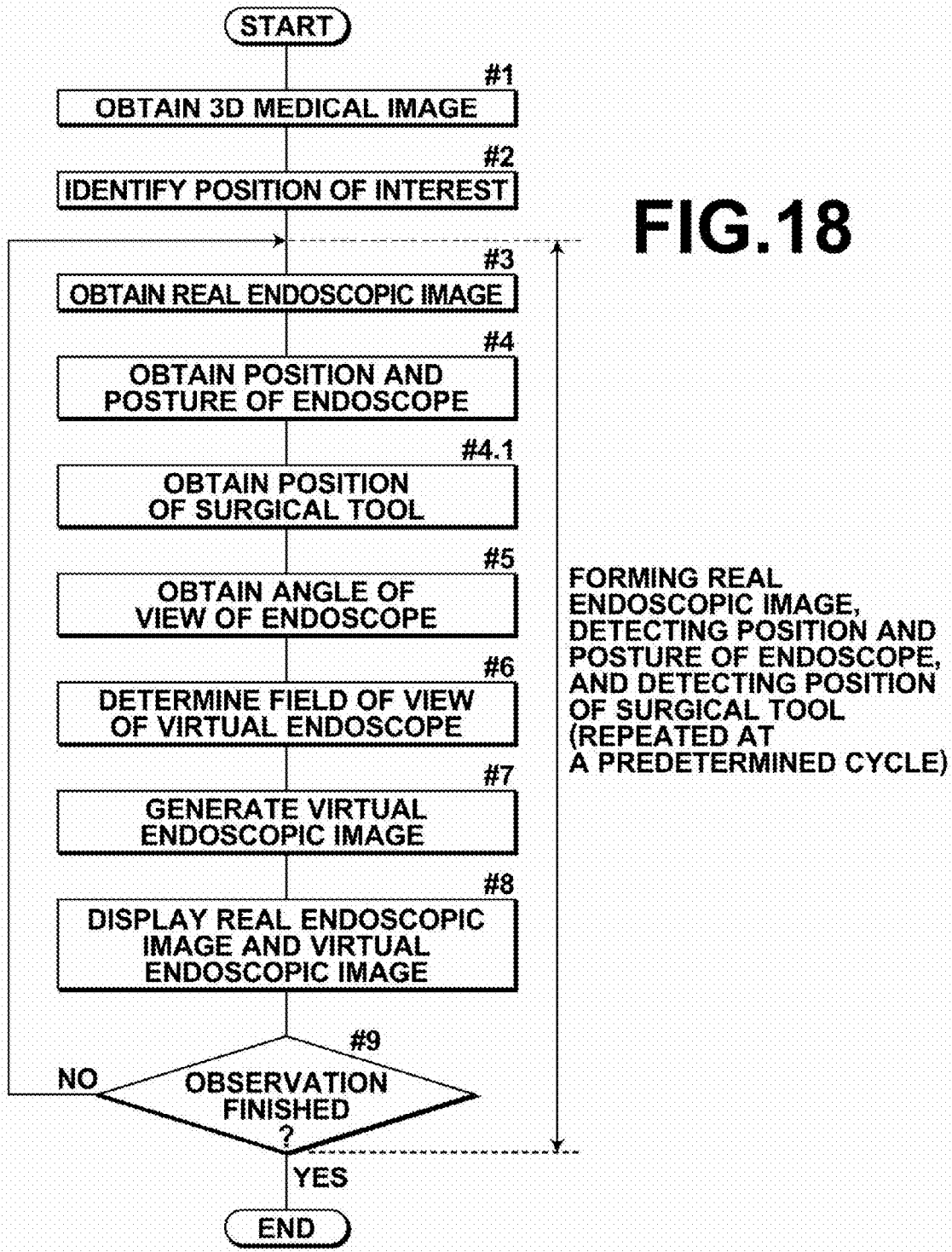
FIG. 18 is a flow chart illustrating the flow of the endoscopic observation support process according to the sixth embodiment of the invention.

FIG. 18 is a flowchart illustrating the flow of an endoscopic observation support process in the sixth embodiment of the invention. As written on the right side of the flow chart, during observation of the interior of abdominal cavity of the subject using the endoscope 1, the real endoscopic image forming unit 2 repeatedly forms the real endoscopic image $I_{RE}$, the endoscope position and posture detecting unit 11 repeatedly detects the position $PS_E$ and the posture $DS_E$ of the endoscope, and the surgical tool position detecting unit 12 repeatedly detects a real-time position $PS_T$ of the surgical tool 6 inserted in the body cavity at predetermined time intervals until the observation ends (#9: YES). Further, after the position and posture of the endoscope are obtained in step #4 of the first embodiment, the surgical tool position obtaining unit 31 obtains the surgical tool position $PS_T$ detected by the surgical tool position detecting unit 12, and outputs a surgical tool position $P_T$, which is obtained by transforming the obtained surgical tool position $PS_T$ into a position in the coordinate system of the 3D medical image V (#4.1).

Then, after the endoscope angle of view obtaining unit 25 obtains the angle of view $A_E$ of the endoscope 1 (#5), the virtual field of view determining unit 26 determines the virtual field of view of the virtual endoscope positioned at the endoscope position $P_E$ based on the position of structure of interest $P_I$, the endoscope position $P_E$, the center line of sight vector $VL_E$, and the angle of view $A_E$, as well as the surgical tool position $P_T$ obtained by the surgical tool position obtaining unit 31, such that the position of structure of interest $P_I$ and the surgical tool position $P_T$ are contained within the virtual field of view and the virtual field of view has continuity with the endoscope-corresponding field of view, which is a field of view of the 3D medical image corresponding to the field of view of the endoscope 1. Then, the virtual field of view determining unit 26 outputs the view point $VP_{VE}$, the center line of sight vector $VL_{VE}$ and the angle of view $A_{VE}$ of the virtual endoscope (#6). When the virtual endoscopic image $I_{VE}$ is generated in the same manner as in the first embodiment, the virtual endoscopic image generating unit 27 generates the virtual endoscopic image $I_{VE}$ which shows that the surgical tool 6 is present at a position corresponding to the surgical tool position $P_T$ in the virtual endoscopic image $I_{VE}$ in an identifiable manner, based on the surgical tool position $P_T$ obtained by the surgical tool position obtaining unit 31 (#7). The flow of the following operations (steps #8 to #9) is the same as that in the first embodiment.

Next, the features unique to this embodiment with respect to the individual processing units are described in detail.

Similarly to the endoscope position obtaining unit 22, the surgical tool position obtaining unit 31 has a function of a communication interface to obtain the surgical tool position $PS_T$ via communication with the surgical tool position detecting unit 12, and a function of transforming the obtained surgical tool position $PS_T$ in the three-dimensional coordinate system of the position sensor 8 into the surgical tool position $P_T$ represented by coordinate values in the three-dimensional coordinate system of the 3D medical image V and storing the surgical tool position $P_T$ in a predetermined memory area of the image processing workstation.

Figure 19A:
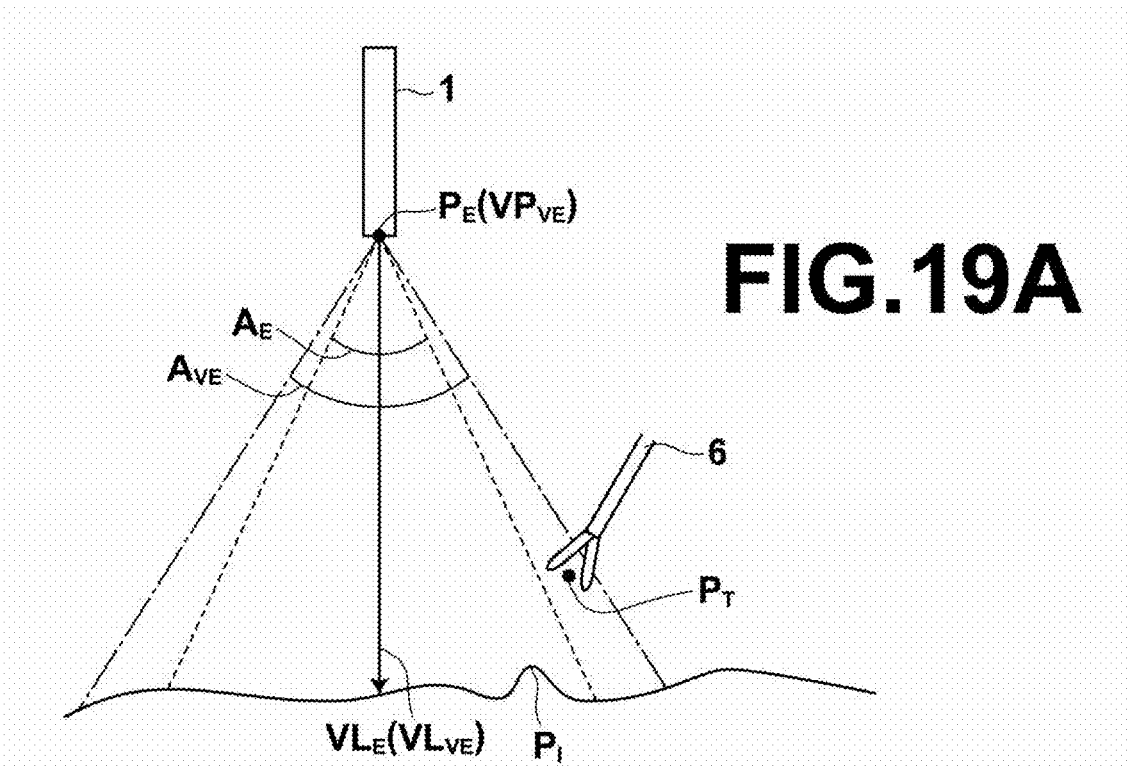
FIG. 19A is a diagram schematically illustrating one example of the field of view of the virtual endoscope, which is determined based on the field of view of the real endoscope and positions of the structure of interest and a surgical tool, in the sixth embodiment of the invention.

As schematically shown in FIG. 19A, similarly to the first embodiment, the virtual field of view determining unit 26 first determines the view point position $VP_{VE}$ of the virtual endoscope to be the same as the endoscope position $P_E$ obtained by the endoscope position and posture obtaining unit 22, and determines the center line of sight vector $VL_{VE}$ of the virtual endoscope to be the same as the center line of sight vector $VL_E$ of the endoscope 1 obtained by the endoscope position and posture obtaining unit 22. Then, the virtual field of view determining unit 26 determines the angle of view $A_{SE}$ of the virtual endoscope to be wider than the angle of view $A_E$ of the endoscope 1 and such that the position of structure of interest $P_I$ and the surgical tool position $P_T$ are contained within the field of view of the virtual endoscope. Specifically, for example, assuming that an angle $\theta_1$ is formed between the center line of sight vector $VL_{VE}$ of the virtual endoscope and a vector connecting the view point position $VP_{VE}$ of the virtual endoscope and the position of structure of interest $P_I$, and an angle $\theta_2$ is formed between the center line of sight vector $VL_{VE}$ of the virtual endoscope and a vector connecting the view point position $VP_{VE}$ of the virtual endoscope and the surgical tool position $P_T$, then, the angle of view $A_{VE}$ of the virtual endoscope may be found by adding a constant to the largest one of the values of the angle of view $A_E$ of the endoscope 1, $2\theta_1$ and $2\theta_2$, or by multiplying the largest one of the values by a predetermined factor larger than 1. In FIG. 19A, the surgical tool position $P_T$ is farther from the center of the field of view than the position of structure of interest $P_I$, and therefore $2\theta_2$ is the largest value.

Similarly to the generation of the virtual endoscopic image $I_{VE}$ in the first embodiment, the virtual endoscopic image generating unit 27 generates a preliminary virtual endoscope image from the 3D medical image V inputted thereto based on the view point position $VP_{VE}$, the center line of sight vector $VL_{VE}$ and the angle of view $A_{VE}$ of the virtual endoscope. Then, the virtual endoscopic image generating unit 27 generates a surgical tool shape image $M_T$, which represents a state where the surgical tool 6 is present at the surgical tool position $P_T$. Specifically, the surgical tool shape image $M_T$ is generated based on an image representing the shape of the surgical tool 6 stored in a database and the surgical tool position $P_T$, as taught in the above-mentioned Patent Document 2. Then, the virtual endoscopic image generating unit 27 combines the surgical tool shape image $M_T$ with the preliminary virtual endoscope image by a known technique, such as alpha blending, to generate the virtual endoscopic image $I_{VE}$. It should be noted that, without generating the surgical tool shape image as described above, a marker, such as an arrow or icon, representing the surgical tool 6 and an annotation, such as a text comment, may be superimposed at a position corresponding to the surgical tool position $P_T$ in the preliminary virtual endoscope image to generate the virtual endoscopic image $I_{VE}$.

Figure 19B:
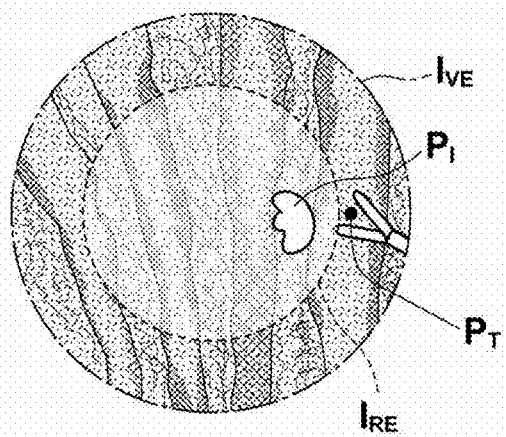
FIG. 19B is a diagram schematically illustrating one example of the superimposed display of the real endoscopic image and the virtual endoscopic image in the sixth embodiment of the invention.

FIG. 19B schematically shows one example of a display screen where the virtual endoscopic image $I_{VE}$ generated in this embodiment and the real endoscopic image $I_{RE}$ are superimposed one on the other. As shown in the drawing, the surgical tool shape image $M_T$ is superimposed at the position corresponding to the surgical tool position $P_T$ in the virtual endoscopic image $I_{VE}$.

As described above, according to the sixth embodiment of the invention, the virtual endoscopic image $I_{VE}$ which contains, in the field of view thereof, not only the position of structure of interest $P_I$ but also the surgical tool position $P_T$ is generated, thereby allowing the user to reliably recognize the relative positional relationship and the relative approach among not only the endoscope 1 and the structure of interest, but also the surgical tool 6.

Further, at this time, the field of view and the image content of the continuously displayed virtual endoscopic image $I_{VE}$ are changed real-time by feedback of the real-time position of the surgical tool 6 detected by the surgical tool position detecting unit 12. This allows the user to dynamically and more appropriately recognize the relative positional relationship and the relative approach among not only the endoscope 1 and the structure of interest, but also the surgical tool 6.

Further, the real endoscopic image forming unit 2 forms the real endoscopic image $I_{RE}$ which represents the interior of the body cavity taken real-time with the endoscope 1, and the real endoscopic image $I_{RE}$ which is formed almost at the same time when the positions of the endoscope 1 and the surgical tool 6 used to generate the virtual endoscopic image $I_{VE}$ are detected is displayed with being superimposed on the virtual endoscopic image $I_{VE}$. Therefore, similarly to the first embodiment, the real endoscopic image $I_{RE}$ and the virtual endoscopic image $I_{VE}$ show the state of the interior of the body cavity almost at the same point of time, and thus the real endoscopic image $I_{RE}$ and the virtual endoscopic image $I_{VE}$ are continuously displayed with being superimposed one on the other in a temporally synchronized manner. Further, at this time, the field of view of the real endoscopic image $I_{RE}$ change along with movement or rotation of the endoscope 1, and the field of view and the image content of the virtual endoscopic image $I_{VE}$ also change along with movement of not only the endoscope 1 but also the surgical tool 6. In this manner, in the sixth embodiment of the invention, the user can observe the interior of the body cavity real-time with complementarily using the real endoscopic image $I_{RE}$ and the virtual endoscopic image $I_{VE}$.

In a seventh embodiment of the invention, the 3D medical image V is formed and obtained real-time during the observation using the endoscope. In this case, the endoscope marker 7a, the surgical tool marker 7b and the position sensor 8 in the hardware configuration of the sixth embodiment (see FIG. 16) are not necessary.

Figure 20:
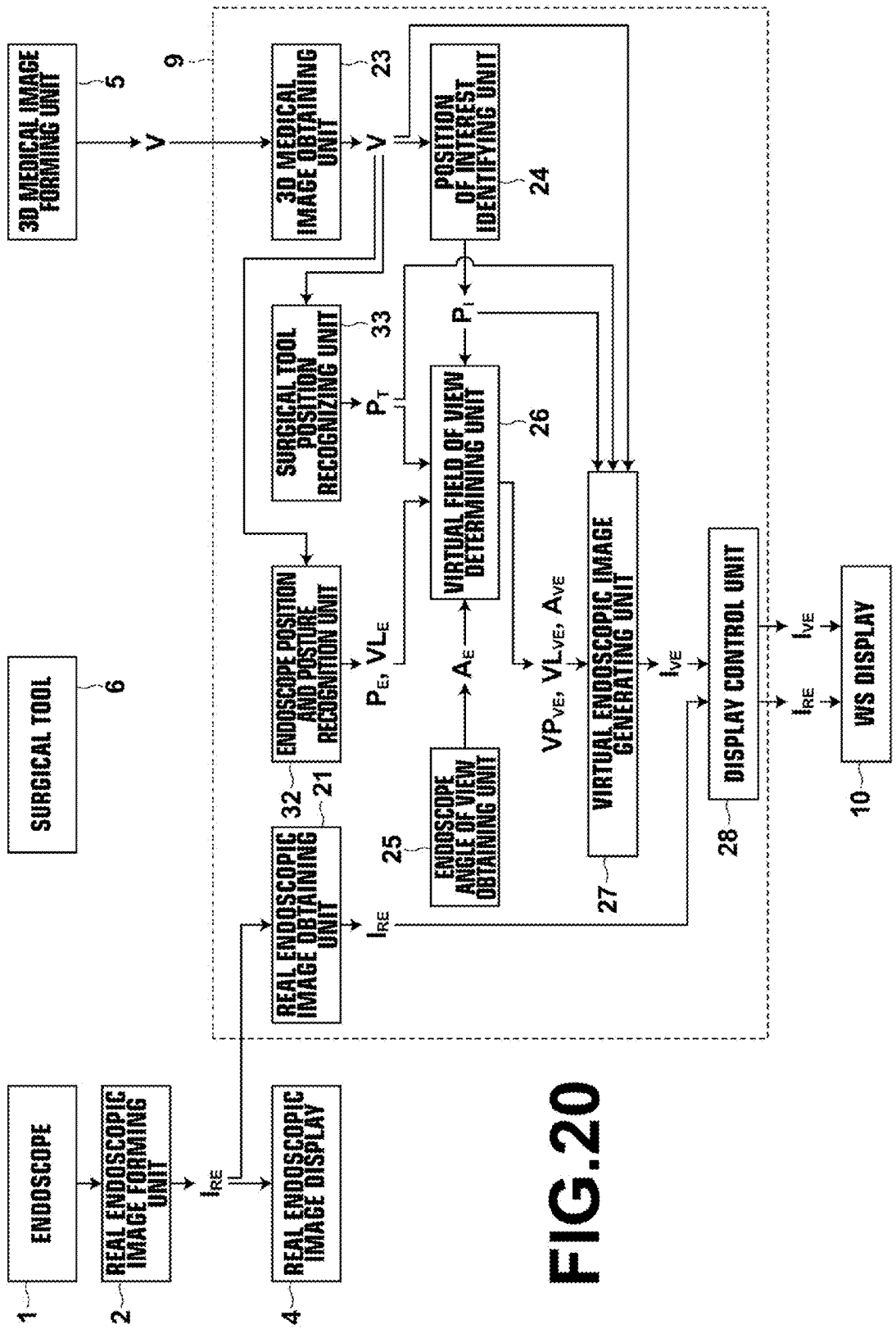
FIG. 20 is a functional block diagram of the endoscopic observation support system according to a seventh embodiment of the invention.

FIG. 20 is a functional block diagram of the endoscopic observation support system according to the seventh embodiment of the invention. As shown in the drawing, the endoscopic observation support system of the seventh embodiment includes an endoscope position and posture recognizing unit 32 and a surgical tool position recognizing unit 33, in place of the endoscope position and posture detecting unit 11, the surgical tool position detecting unit 12, the endoscope position and posture obtaining unit 22 and the surgical tool position obtaining unit 31 of the sixth embodiment. That is, the endoscope position and posture recognizing unit 32 and the surgical tool position recognizing unit 33 correspond to the position (and posture) detecting means of the invention.

The endoscope position and posture recognizing unit 32 and the surgical tool position recognizing unit 33 are processing units implemented on the image processing workstation 9. The endoscope position and posture recognizing unit 32 and the surgical tool position recognizing unit 33 extract regions showing the endoscope 1 and the surgical tool 6, respectively, from the 3D medical image V inputted thereto to recognize the endoscope position $P_E$ and the posture $VL_E$, and the surgical tool position $P_T$, respectively, using known pattern recognition processing.

Figure 21:
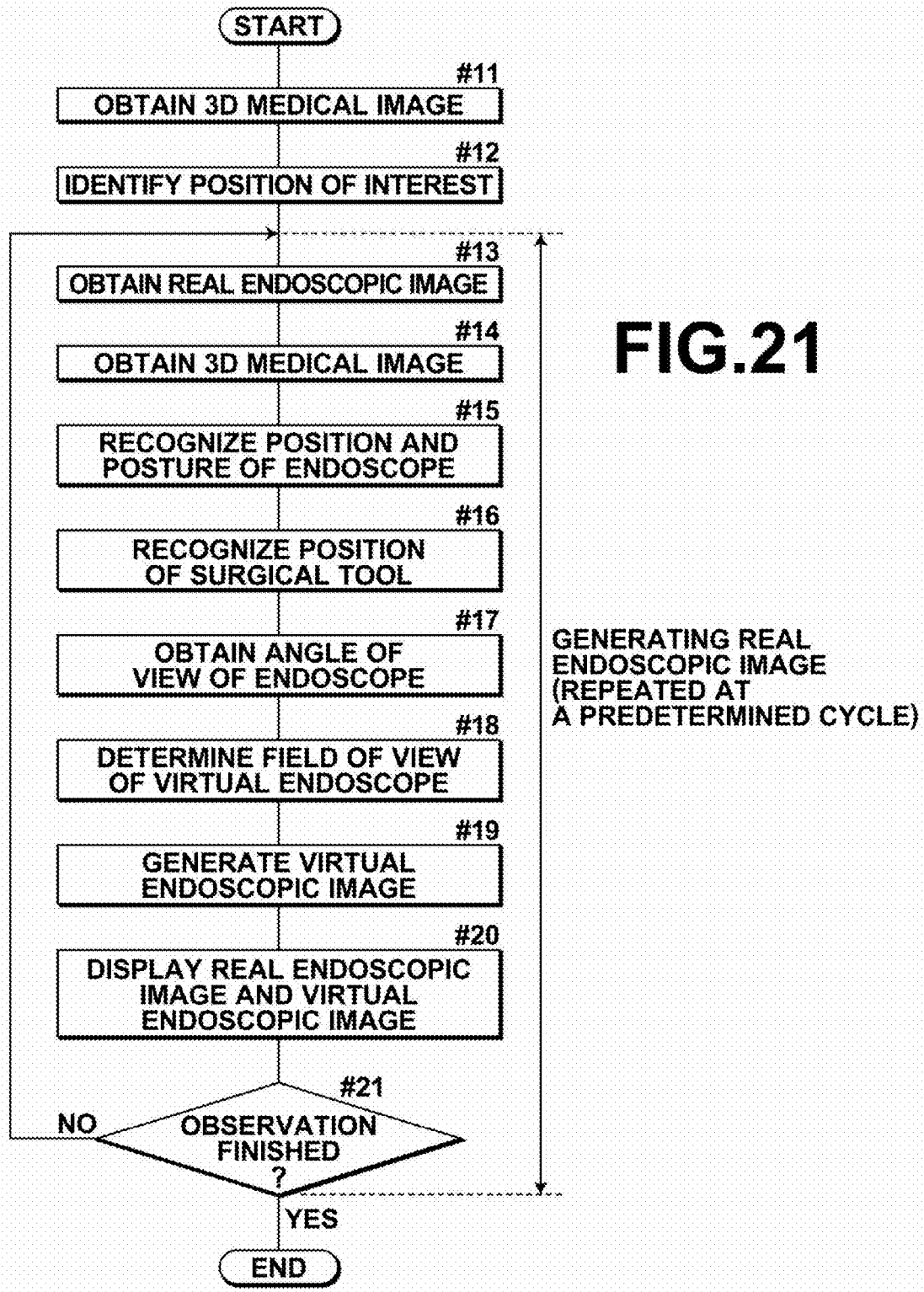
FIG. 21 is a flow chart illustrating the flow of the endoscopic observation support process in the seventh embodiment of the invention.

FIG. 21 is a flow chart illustrating the flow of the endoscopic observation support process according to the seventh embodiment of the invention. As shown in the drawing, steps #11 to #13 are the same as steps #1 to #3 of the sixth embodiment, and then, the 3D medical image obtaining unit 23 obtains the 3D medical image V (#14). Then, the endoscope position and posture recognizing unit 32 recognizes the endoscope position $P_E$ and the posture $VL_E$ (#15) and the surgical tool position recognizing unit 33 recognizes the surgical tool position $P_T$ (#16) based on the 3D medical image V obtained by the 3D medical image obtaining unit 24. The following steps #17 and #18 are the same as steps #5 and #6 of the sixth embodiment. Then, in step #19, the virtual endoscopic image generating unit 27 generates the virtual endoscopic image $I_{VE}$ using a color template that is defined such that the region showing the surgical tool 6 extracted by the surgical tool position recognizing unit 33 is displayed in a predetermined color. Therefore, it is not necessary to generate the shape image of the surgical tool 6 as in the sixth embodiment. Steps #20 and #21 are the same as steps #8 and #9 of the sixth embodiment.

By forming and obtaining the 3D medical image V real-time during the observation using the endoscope in this manner, the obtained 3D medical image V shows the state of the interior of the abdominal cavity almost at the same point of time as that shown in the real endoscopic image $I_{RE}$. Therefore, the generated virtual endoscopic image $I_{VE}$ more accurately shows the real-time state of the interior of the abdominal cavity than a case where the 3D medical image V obtained before the endoscopic observation is used. It should be noted that, when the 3D medical image V is taken in steps #11 and #14 of this embodiment, it is necessary to pay attention to the posture of the subject during imaging so that the position of the subject corresponding to the origin of the coordinate axes and the orientation of the coordinate axes are not changed.

In the seventh embodiment of the invention, it is preferable to use an ultrasound diagnostic device as the modality 5, in view of reducing radiation exposure of the subject.

The above-described embodiments are merely examples and should not be construed as limiting the technical scope of the invention.

Further, variations and modifications made to the system configuration, the hardware configuration, the process flow, the module configuration, the user interface and the specific contents of the process of the above-described embodiments without departing from the scope and spirit of the invention are also within the technical scope of the invention.

For example, with respect to the system configuration, although the modality 5 is directly connected to the image processing workstation 9 in the hardware configuration of FIG. 1 or 6 of the above-described embodiments, an image storage server may be connected to the LAN, and the 3D medical image V formed by the modality 5 may once be stored in a database of the image storage server, so that the 3D medical image V is transferred from the image storage server to the image processing workstation 9 in response to a request from the image processing workstation 9.

The endoscope 1 may not be a hard endoscope, and a soft endoscope or a capsular endoscope may be used.

As the modality 5, besides the above-mentioned CT device and the ultrasound diagnostic device, a MRI device, etc., may be used.

The WS display 10 may be a display that supports known stereoscopic display to display the virtual endoscopic image $I_{VE}$ which is formed as a stereoscopic image. For example, in a case where the WS display 10 is a display device that achieves stereoscopic display using two parallax images for the right and left eyes, the virtual endoscopic image generating unit 27 may generate virtual endoscope parallax images for the right and left eyes by setting positions of the right and left eyes, which are shifted from the view point position $VP_{VE}$ by an amount of parallax between the right and left eyes, and performing perspective projection with using the thus set right and left eye positions as the view points. Then, the display control unit 28 may exert control such that display pixels of the WS display 10 for the left eye to display the virtual endoscope parallax image for the left eye and display pixels of the WS display 10 for the right eye to display the virtual endoscope parallax image for the right eye.

The endoscope position and posture detecting unit 11 and the surgical tool position detecting unit 12 may use a magnetic system, or may use a gyro or a rotary encoder, as taught in Patent Document 2.

The body site to be observed may be a site of the subject which is suitable for observation using an endoscope, such as the interior of the thoracic cavity, other than the interior of the abdominal cavity.

In the above-described embodiments, the image processing workstation 9 receives the image based on a request from the real endoscopic image obtaining unit 21 with taking the communication load into account, assuming that a cycle at which the real endoscopic image forming unit 2 forms the real endoscopic image $I_{RE}$ is shorter than a cycle at which the virtual endoscopic image generating unit 27 generates the virtual endoscopic image $I_{VE}$. However, the real endoscopic image obtaining unit 21 may receive all the real endoscopic images IE sequentially formed by the real endoscopic image forming unit 2. In this case, the display control unit 28 may update the displayed real endoscopic image $I_{RE}$ on the WS display 10 each time the real endoscopic image $I_{VE}$ is received, asynchronously with the timing of generation of the virtual endoscopic image $I_{VE}$ by the virtual endoscopic image generating unit 27.

The endoscope position and posture obtaining unit 22 may receive all the endoscope positions $PS_E$ detected at predetermined time intervals by the endoscope position and posture detecting unit 11, and may transform only the endoscope position $PS_E$ which is received at the time when the operation in step #4 of FIG. 3 is invoked into the endoscope position $P_E$ by the coordinate transformation function to output it. The same applies to the surgical tool position obtaining unit 31.

The coordinate transformation carried out by the endoscope position and posture obtaining unit 22 and the surgical tool position obtaining unit 31 in the above-described embodiments may be carried out by the virtual endoscopic image generating unit 27.

The position of interest identifying unit 24 may automatically identify the position of interest using a known image recognition technique (such as a technique for extracting blood vessels or an organ, or a technique for detecting an abnormal shadow).

The virtual endoscopic image generating unit 27 may further generate virtual endoscopic images viewed from a plurality of view points by setting a plurality of positions of interest, such as a site of surgical interest, an attention-required blood vessel, an attention-required organ and a surgical tool, as the view points.

The invention claimed is:

1. An endoscopic observation support system comprising:
a 3D medical image forming unit configured to form a 3D medical image representing an interior of a body cavity of a subject;
a position of interest identifying unit configured to identify a position of a structure of interest in the body cavity in the 3D medical image;
an endoscope position and posture detecting unit configured to detect a real-time position and a real-time posture of an endoscope inserted in the body cavity;
an endoscope angle of view obtaining unit configured to obtain information of an angle of view of the endoscope;
a virtual field of view determining unit configured to determine a virtual field of view of a virtual endoscope positioned at an endoscope-corresponding position, the endoscope-corresponding position being a position in the 3D medical image corresponding to the detected position of the endoscope, based on the identified position of the structure of interest, the detected position and posture of the endoscope in the 3D medical image, and the angle of view of the endoscope, such that the position of the structure of interest is contained within the virtual field of view and the virtual field of view has continuity with an endoscope-corresponding field of view, the endoscope-corresponding field of view being a field of view of the 3D medical image corresponding to a field of view of the endoscope;
a virtual endoscopic image generating unit configured to generate, from the 3D medical image inputted thereto, a virtual endoscopic image having the virtual field of view with a view point thereof being the endoscope-corresponding position;
a display control unit configured to cause a display unit to display the virtual endoscopic image; and
a real endoscopic image forming unit configured to form a real endoscopic image representing the interior of the body cavity by real-time imaging with the endoscope,
wherein the display control unit causes the virtual endoscopic image and the real endoscopic image which is formed almost at the same time when the position and posture of the endoscope used to generate the virtual endoscopic image are detected to be displayed with being superimposed a part of the real endoscopic image on a part of the virtual endoscopic image which is the same area of an organ in the interior of the body cavity that is represented in the virtual endoscopic image as the area of the organ in the interior of the body cavity that is represented in the real endoscopic image.

2. The endoscopic observation support system as claimed in claim 1, wherein the virtual endoscopic image generating unit generates the virtual endoscopic image in which the structure of interest is shown in an identifiable manner.

3. The endoscopic observation support system as claimed in claim 1, wherein the virtual endoscopic image generating unit determines pixel values of the virtual endoscopic image depending on a distance from the position of the endoscope to a surface of a structure in the body cavity.

4. The endoscopic observation support system as claimed in claim 1, further comprising a warning unit configured to show a warning when an approach of the endoscope to the structure of interest satisfies a predetermined criterion.

5. The endoscopic observation support system as claimed in claim 1, wherein the virtual endoscopic image generating unit determines pixel values of the virtual endoscopic image using a color template, wherein the color template is defined to provide the virtual endoscopic image showing sites in the body cavity in almost the same appearance as those shown in the real endoscopic image obtained by imaging with the endoscope.

6. The endoscopic observation support system as claimed in claim 1, further comprising
a second position of interest identifying unit configured to identify a position of a second structure of interest in the body cavity in the 3D medical image,
wherein the virtual endoscopic image generating unit generates the virtual endoscopic image in which the second structure of interest is shown in an identifiable manner.

7. The endoscopic observation support system as claimed in claim 6, wherein the structure of interest is a site of surgical interest during endoscopic surgery using the endoscope and the second structure of interest is an anatomical structure that requires attention during the endoscopic surgery.

8. The endoscopic observation support system as claimed in claim 6, wherein the structure of interest is a site of surgical interest during endoscopic surgery using the endoscope, and the second structure of interest is a surgical tool inserted in the body cavity.

9. The endoscopic observation support system as claimed in claim 1, wherein the structure of interest is a site of surgical interest during endoscopic surgery using the endoscope.

10. The endoscopic observation support system as claimed in claim 1, wherein the structure of interest is an anatomical structure that requires attention during endoscopic surgery using the endoscope.

11. The endoscopic observation support system as claimed in claim 1, wherein the structure of interest is a surgical tool inserted in the body cavity.

12. An endoscopic observation support system comprising:
a 3D medical image forming unit configured to form a 3D medical image representing an interior of a body cavity of a subject;
a position of interest identifying unit configured to identify a position of a structure of interest in the body cavity in the 3D medical image;
an endoscope position and posture detecting unit configured to detect a real-time position and a real-time posture of an endoscope inserted in the body cavity;
an endoscope angle of view obtaining unit configured to obtain information of an angle of view of the endoscope;
a virtual field of view determining unit configured to determine a virtual field of view of a virtual endoscope positioned at an endoscope-corresponding position, the endoscope-corresponding position being a position in the 3D medical image corresponding to the detected position of the endoscope, based on the identified position of the structure of interest, the detected position and posture of the endoscope in the 3D medical image, and the angle of view of the endoscope, such that the position of the structure of interest is contained within the virtual field of view and the virtual field of view has continuity with an endoscope-corresponding field of view, the endoscope-corresponding field of view being a field of view of the 3D medical image corresponding to a field of view of the endoscope;
a virtual endoscopic image generating unit configured to generate, from the 3D medical image inputted thereto, a virtual endoscopic image having the virtual field of view with a view point thereof being the endoscope-corresponding position; and
a display control unit configured to cause a display unit to display the virtual endoscopic image,
wherein the virtual field of view determining unit determines the virtual field of view such that an angle of view of the virtual endoscope is wider than the angle of view of the endoscope.

13. An endoscopic observation support method comprising the steps of:
forming a 3D medical image representing an interior of a body cavity of a subject before or during endoscopic observation of the interior of the body cavity with an endoscope inserted in the body cavity;
identifying a position of a structure of interest in the body cavity in the 3D medical image;
detecting a real-time position and a real-time posture of the endoscope inserted in the body cavity;
obtaining information of an angle of view of the endoscope;
determining a virtual field of view of a virtual endoscope positioned at an endoscope-corresponding position, the endoscope-corresponding position being a position in the 3D medical image corresponding to the detected position of the endoscope, based on the identified position of the structure of interest, the detected position and posture of the endoscope in the 3D medical image, and the angle of view of the endoscope, such that the position of the structure of interest is contained within the virtual field of view and the virtual field of view has continuity with an endoscope-corresponding field of view, the endoscope-corresponding field of view being a field of view of the 3D medical image corresponding to a field of view of the endoscope;
generating, from the 3D medical image inputted, a virtual endoscopic image having the virtual field of view with a view point thereof being the endoscope-corresponding position, the virtual endoscopic image representing the interior of the body cavity viewed from the view point; and
displaying the virtual endoscopic image,
wherein the virtual field of view determining determines the virtual field of view such that an angle of view of the virtual endoscope is wider than the angle of view of the endoscope.

14. An endoscopic observation support device comprising:
a 3D medical image obtaining unit configured to obtain a 3D medical image representing an interior of a body cavity of a subject;
a position of interest identifying unit configured to identify a position of a structure of interest in the body cavity in the 3D medical image;
a position and posture obtaining unit configured to obtain a real-time position and a real-time posture of an endoscope inserted in the body cavity detected by a position and posture detecting unit;
an endoscope angle of view obtaining unit configured to obtain information of an angle of view of the endoscope;
a virtual field of view determining unit configured to determine a virtual field of view of a virtual endoscope positioned at an endoscope-corresponding position, the endoscope-corresponding position being a position in the 3D medical image corresponding to the detected position of the endoscope, based on the identified position of the structure of interest, the obtained position and posture of the endoscope in the 3D medical image, and the angle of view of the endoscope, such that the position of the structure of interest is contained within the virtual field of view and the virtual field of view has continuity with an endoscope-corresponding field of view, the endoscope-corresponding field of view being a field of view of the 3D medical image corresponding to a field of view of the endoscope;

a virtual endoscopic image generating unit configured to generate, from the 3D medical image inputted thereto, a virtual endoscopic image having the virtual field of view with a view point thereof being the endoscope-corresponding position; and a display control unit configured to cause a display unit to display the virtual endoscopic image, wherein the virtual field of view determining unit determines the virtual field of view such that an angle of view of the virtual endoscope is wider than the angle of view of the endoscope.

15. A non-transitory computer readable medium containing an endoscopic observation support program for causing a computer to carry out the steps of:

obtaining a 3D medical image representing an interior of a body cavity of a subject;

identifying a position of a structure of interest in the body cavity in the 3D medical image;

obtaining a real-time position and a real-time posture of an endoscope inserted in the body cavity detected by a position and posture detecting unit;

obtaining information of an angle of view of the endoscope;

determining a virtual field of view of a virtual endoscope positioned at an endoscope-corresponding position, the endoscope-corresponding position being a position in the 3D medical image corresponding to the detected position of the endoscope, based on the identified position of the structure of interest, the detected position and posture of the endoscope in the 3D medical image, and the angle of view of the endoscope, such that the position of the structure of interest is contained within the virtual field of view and the virtual field of view has continuity with an endoscope-corresponding field of view, the endoscope-corresponding field of view being a field of view of the 3D medical image corresponding to a field of view of the endoscope;

generating, from the 3D medical image inputted, a virtual endoscopic image having the virtual field of view with a view point thereof being the endoscope-corresponding position; and causing a display unit to display the virtual endoscopic image, wherein the virtual field of view determining determines the virtual field of view such that an angle of view of the virtual endoscope is wider than the angle of view of the endoscope.

* * * * *